United States Patent [19]
Green et al.

[11] Patent Number: 6,127,340
[45] Date of Patent: Oct. 3, 2000

[54] SERINE PROTEASE INHIBITORS

[75] Inventors: Donovan St. Clair Green; Said Mohammed Anwr Ahmed Elgendy; Geeta Patel, all of London; Michael Finbar Scully, Essex; Christopher Andrew Goodwin, Avon; Vijay Vir Kakkar, Hants; John Joseph Deadman, Surrey, all of United Kingdom

[73] Assignee: Trigen Limited, London, United Kingdom

[21] Appl. No.: 08/894,120

[22] PCT Filed: Feb. 15, 1996

[86] PCT No.: PCT/GB96/00352

§ 371 Date: Mar. 30, 1998

§ 102(e) Date: Mar. 30, 1998

[87] PCT Pub. No.: WO96/25427

PCT Pub. Date: Aug. 22, 1996

[30]  Foreign Application Priority Data

Feb. 16, 1995 [GB] United Kingdom .................. 9502985

[51] Int. Cl.⁷ .......................... A61K 38/00; A61K 38/02; C07K 5/00; C07K 7/00

[52] U.S. Cl. ................................. 514/18; 514/19; 514/20; 530/300; 530/331; 530/332

[58] Field of Search .................................. 514/18, 19, 20; 530/300, 331, 332

[56]  References Cited

FOREIGN PATENT DOCUMENTS

| WO 92/07869 | 5/1992 | WIPO . |
| WO 94/20526 | 9/1994 | WIPO . |
| 9525427 | 8/1996 | WIPO .............................. C07K 5/06 |

*Primary Examiner*—Avis M. Davenport
*Attorney, Agent, or Firm*—Townsend and Townsend and Crew LLP

[57]  ABSTRACT

This invention is directed to peptide inhibitors of serine proteases, espcecially thrombin, in which the P1-P2 natural amide linkage is replaced by another bond. Exemplary thrombin inhibitors have the formula: $X\text{-}(aa^3)\text{-}(aa^2)\text{-}\psi\text{-}(aa^1)\text{-}Z$ wherein X is H or a substituent on the N-terminal amino group, $aa^3$ is a hydrophobic amino acid, $aa^{23}$ is Pro, $aa^1$ is Arg or an Arg analgoue, Z is —COOH or a heteroatom acid group and $\psi$ is a non-amide linkage.

56 Claims, No Drawings

SERINE PROTEASE INHIBITORS

This invention relates to enzyme inhibitors and enzyme substrates, particularly those of trypsin-like or chymotrypsin-like enzymes, and to their use for example in the treatment or prevention of thrombosis.

Cardiovascular disease is a major cause of mortality, with incidence across the world higher than that of cancer. Acute events in the disease state, such as myocardial infarction, stroke, peripheral arterial occlusion and venous thromboembolic disease have recently been understood to be precipitated by formation of thromboembolic clots. This clot formation, as well as the aetiology of the disease state, e.g. formation of atheromatous plaque, has been shown to be mediated by the coagulation serine protease enzymes which control also the normal haemostatic balance of the blood. Modulation of any one coagulation protease, especially Factor VIIa. Factor Xa or thrombin, has been shown to control thrombogenesis. This has led to the development of inhibitors of serine protease enzymes to prevent thrombotic events in the clinic.

The family of serine protease enzymes all cleave peptide bonds by a mechanism involving the catalytic triad of Asp-His-Ser residues in the active site of the enzymes. Serine protease inhibitors have been designed which use functional groups, e.g. CO—H, $B(OH)_2$, $P(O)(OR)_2$, beta lactam, chloromethylketone, to interact with the triad and thereby block activation of the substrates.

However, serine proteases (Protein C. Plasmin) are also involved in thrombolysis and other physiological pathways, and broad inhibition of the coagulation serine proteases has been shown to be difficult to control. Thus, it can be desirable to make inhibitors selective for one target protease. Such selective inhibitors have been prepared by making peptide inhibitors comprising peptide sequences that bind preferentially to subsites unique in the target protease. Typically these sequences mimic the structure around the scissile bond of the natural substrate of the protease, which is fibrinogen in the case of thrombin. For example, selective peptide inhibitors of thrombin typically incorporate a sequence based on Phe-Pro, or more generally (aa)-Pro, where (aa) is some hydrophobic amino acid or analogue thereof The amino acid residue which provides the carbonyl group of the scissile bond of a peptide sequence is designated "P1". Successive amino acid residues on the N-terminal side of residue P1 are designated P2, P3, P4, . . . etc; amino acid residues on the C-terminal side of residue P1 are designated P1', P2', P3'. . . . In fibrinogen, P1' is glycine and P2' is proline. The protease contains a "specificity pocket" which recognises the side chain of the P1 amino acid. Thrombin belongs to a family of serine protease inhibitors described as "trypsin-like": the trypsin-like proteases normally recognise P1 residues with arginine-like or serine-like side chains. There is also a chymotrypsin-like family of serine protease inhibitors whose specificity pocket recognises phenylalanine-like and alanine-like side chains on the P1 residue.

Peptide inhibitors of serine proteases have been made in which the P1 terminal carboxy group is replaced by another acid group, e.t. a boronic acid group or a phosphorus oxyacid function. The P1 terminal carboxy or heteroatom analogue group may be derivatised, for example to form an ester, an alcohol, a thiol or an amine or to replace the OH groups of boronic acid with fluorine. The identity of the derivative moiety is not critical and may be selected according to the desired use of the target compound. Peptide inhibitors having a boron or phosphorus heteroatom analogue group at the P1 residue are described in, for example, WO 92/07869 and EP 0471651. Included herein by reference is U.S. Pat. No. 5,288,707, which is equivalent to EP 0471651 as well as U.S. Ser. No. 08/317,837 derived from WO 92/07869. Inhibitors having a P1 sulphonic acid group and derivatives thereof are described in Wong, S. C., Green, G. D. J., and Shaw, E., *J.Med.Chem.,* 1978, 21, 456–459. Inactivation of trypsin-like serine proteases by sulfonylation. Variation of the positively charged group and inhibitor length. As examples of such peptide serine protease inhibitors, it may be mentioned that α-amino boronic acid peptides have been prepared because of the favourable binding energy of the interaction of boron with a nucleophile, such as the lone pair of the Ser hydroxyl or His imidazole group, to give a tetrahedral boronate intermediate which mimics the shape of the "transition state" formed during substrate cleavage and so is tightly bound to the enzyme. The α-amino group of such α-amino boronic acid compounds forms the P1-P2 amide link of the peptide.

The literature teaches that a broad range of serine proteases are strongly inhibited by α-aminoboronic acid-containing peptides; Tapparelli, C.; Metternich, R.; Erhardt, C.; Zurini, M.; Claeson, G. Scully; M. F.; Stone, S. R. "In Vitro and In Vivo Characterisation of a Neutral Boron-containing Thrombin Inhibitor" *J.Biol.Chem.* 1993, 268, 4734–4741; Boroarginine Thrombin Inhibitors' Kettner, C., Mersinger, L., & Knabb, R. (1990) *J. Biol.Chem.* 265, 18289–18297: Kettner, C. A.; Shenvi, A. B. "Inhibition of the Serine Proteases Leukocyte Elastase, Pancreatic Elastase, Cathepsin G. and Chymotrypsin by Peptide Boronic Acids"; Taparelli, C.; Metternich, R., Erhardt, C.; Cook, N. S. "Synthetic Low-Molecular Weight Thrombin Inhibitors: Molecular Design and Pharmacological Profile" *Trends Pharm.Sci.* 1993, 14, 366–376.

The studies of Kettner have shown that the strongest interactions, intimated by the best observed inhibition constants, are achieved by "substrate-like" inhibitors where the boron interacts with the active site serine, while "non-substrate-like" inhibitors, where the boron interacts only with the active site histidine, bind more weakly. Clearly the binding interactions at the subsites determine the geometry of the active site group, where the amide bond between the P2 and P1 groups confers a rigid "amide plane" geometry on the system, with usually trans orientation of substituents and typically 1.3 Å CO—NH bond lengths.

The literature also teaches that the α-amino group is critical to the activity of peptide inhibitors. and forms a hydrogen bond to the inhibited enzyme, e.g. P1-α-amino of PPACK, NAPAP or MQPA to Gly-216 of thrombin (Bauer, M., Brandsetter, H.; Turk, D.; Sturzebecher, J. and Bode, W. (1993). Seminars in Thrombosis and Haemostasis, 19, 352–360).

EP 0118280 and equivalent U.S. Pat. Nos. 4,638,047 and 4,772,686 describe peptide thrombin inhibitors comprising amino acid residues on the C-terminal side of the scissile bond in which the P1-P1[1] scissile peptide bond is replaced by a non-hydrolysable isosteric linkage, namely —$COCH_2$—, —$CHOHCH_2$— or $CH_2NH$—.

The state of the art, therefore, includes peptide serine protease inhibitors. It will be understood that the term "peptide" includes peptide analogues. Such inhibitors are known to have at the carboxy position of the P1 residue an optionally derivatised carboxy group or an optionally derivatised heteroatom analogue of a carboxy group.

In terms of chemical structure, it may be said that the prior art comprises compounds included in the formula

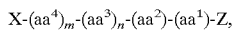

wherein aa$^1$, aa$_2$, and aa$^3$ represent natural or unnatural acid residues and (aa$^4$)$_m$ one or more optional amino acid residues linked to the amino group of aa$^3$. Alternatively any one or more aa groups may be analogues of amino acid residues in which the α-hydrogen is replaced by a substituent. X represents H or a substituent on the N-terminal amino group, Z is —COOH or a C-terminal extension group (carboxy replacement group), for example as known in the art. In preferred compounds, Z is a heteroatom acid group, e.g. —B(OH)$_2$, —P(OH)$_2$ or PO(OH)$_2$, or a derivative thereof, for example a carboxylic acid ester, a dioxo-boronate [—B(Osubstituent)$_2$] or a phosphate [—PO(Osubstituent)$_2$] or BF$_2$. Preferred heteroatom analogue groups are —B(OH)$_2$ and —P(O)(OM)$_2$; a less preferred heteroatom analogue group is S(O)$_2$OH.

Derivatives of the acid groups include those in which inert organic groups, typically containing no more than 20 carbon and hetero-atoms, replace the hydrogen of any acid —OH group; the inert organic groups may be joined to the acid group through the intermediary of a functional group, such as carbonyl or amino, for example. In other derivatives, an —OH group is replaced by a substituent which may, for example, be an inert organic group or halogen, notably fluorine. It is also known to make compounds in which the acid —OH groups are replaced by —SH groups, which may be substituted, or amine groups. Representative inert organic substituents are hydrocarbyl and hydrocarbyl substituted by halogen or —OH; the hydrocarbyl moiety may contain an ether or ester linkage, for example.

The present invention provides novel peptidyl serine protease inhibitors in which the P2-P1 natural peptide linkage is replaced by another linking moiety other than an N-substituted P2-P1 natural peptide linkage.

The invention enables the provision of compounds having beneficial properties as inhibitors of serine proteases and favourable subsite interactions, and retaining geometry suitable for binding at the active site of the enzyme. It also enables the provision of compounds with different combinations of properties compared to prior art compounds, thereby providing the benefit of choice.

In another aspect, the invention provides compounds of the formula I:

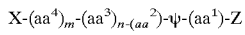  I, wherein, the aforegoing symbols are as defined below, in which definitions "aryl" encompasses heteroaryl and "alkyl" encompasses cycloalkyl:

X is H or an amino protecting group and is bonded to the amino group of the N-terminal amino acid;

m is an integer of from 0 to 5;

n is 0 or 1, provided that if n and m are both 0 then X is a group of the formula R$^{10}$(CH$_2$)$_e$COO— or R$^{10}$(CH$_2$)$_e$SO$_2$— wherein e is 0 to 3 and R$^{10}$ is a C$_5$–C$_{12}$ aryl, arylalkyl or alkylaryl group optionally substituted by halogen or —OH;

ψ is —CO$_2$—, —CH$_2$O—, —NHCO—, —CHYCH$_2$—, —CH=CH—, —CO(CH$_2$)$_p$CO— where p is 1, 2 or 3, —COCHY—, —CO$_2$—CH$_2$NH—, —CHY—NX—, —N(X)CH$_2$N(X)CO—, —CH=C(CN)CO—, —CH(OH)—NH—, —CH(CN)—NH—, —CH(OH)—CH$_2$— or —NH—CHOH—, where X is H or an amino protecting group and Y is H or F;

aa$^1$, aa$^2$, aa$^3$ and aa$^4$ are each independently a residue of a natural or an unnatural amino acid or a group of the formula

—HN—C(W$^1$)(W$^2$)—CO— wherein

W$^1$ and W$^2$ are each independently selected from

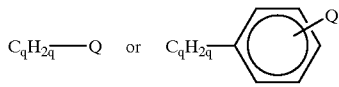 (i)

where Q=amino, amidino, imidazole, guanidino, N$_3$, or isothioureido, and q is an integer of from 1 to 5;

(ii) a side chain of a natural amino acid; or (iii) a group of the formula V or VI:

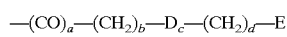 V

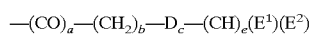 VI wherein a is 0 or 1;

e is 1;

b and d are independently 0 or an integer such that (b+d) is from 0 to 4; and (b+e) is from 1 to 4;

c is 0 or 1;

D is O or S;

E is H, C$_{1-C6}$ alkyl, or a saturated or unsaturated cyclic group which is a 5–6 membered ring, or an 8–14 membered fused ring system, which alkyl or cyclic group is optionally substituted by up to 3 groups independently selected from —R$^{13}$, —R$^1$OR$^{13}$, —R$^1$COR$^{13}$, —R$^1$CO$_2$R$^{13}$ and —R$^1$O$_2$CR$^{13}$, wherein R$^1$ is —(CH$_2$)$_f$— and R$^{13}$ is —(CH$_2$)$_g$H or a moiety which has a total number of carbon and heteroatoms from 5 to 10 and which contains a ring system and optionally an alkyl and/or an alkylene group, wherein f and g are each independently from 0 to 10, provided that (f+g) does not exceed 10, and provided that there is only a single substituent if the substituent group is a said moiety containing a ring system, or E is C$_1$–C$_6$ trialkylsilyl; and E$^1$ and E$^2$ are each independently a 5 or 6 membered ring; in which group of Formula V or VI any one or more hydrogen atoms bonded to a carbon atom is optionally replaced by halogen;

or wherein W$^1$ and W$^2$ together with the carbon atom to which they are bonded form a ring system, W$^1$ and W$^2$ together form an alkenyl or aralkenyl group, or —HNC(W$^1$)(W$^2$)CO— is the residue of an amino acid in which W$^1$ is H and W$^2$ is a group which together with the α-amino group forms a cyclic group which is a 4–6 membered ring or an 8–10 membered fused ring system optionally substituted by up to 3 groups independently selected from —R$^{13}$, —R$^1$OR$^{13}$, —R$^1$COR$^{13}$, —R$^1$CO$_2$R$^{13}$ and —R$^1$O$_2$CR$^{13}$, wherein R$^1$ and R$^{13}$ are as hereinbefore defined and any one or more hydrogen atoms bonded to a carbon atom is optionally replaced by halogen; and

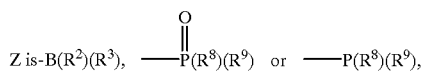

where: R$^2$ and R$^3$ are each independently selected from halogen, —OH, —OR$^4$ and —NR$^4$R$^5$, where R$^4$ and R$^5$ are each independently a group of the formula R$^6$(CO)$_u$—, wherein u is 0 or 1 and R$^6$ is H or an optionally halogenated alkyl, aryl or arylalkyl group containing up to (10-u) carbon atoms and optionally substituted by one or more groups selected from OH, $R^7(CO)_vO—$ and $R^7(CO)_v—$, wherein v is 0 or 1 and $R^7$ is $C_1–C_{6-v}$ alkyl, or is an aryl, alkylaryl, arylalkyl or alkylarylalkyl group containing up to (10-v) carbon atoms, or $R^2$ and $R^3$ taken together represent a residue of a diol or a dithiol;

$R^7$ and $R^8$ and are each independently selected from the group consisting of $R^2$, $R^3$, $R^4$ and $R^5$; and $R^9$ is a group selected from the following: —H, —$OR^4$, $OR^5$, provided that when $aa^1$ is glycine, then $aa^2$ is not a group of the formula —$HNC(W^1)(W^2)CO$— wherein one of $W^1$ and $W^2$ is a group as defined in clause (i) above.

A third aspect of the invention resides in compounds of the formula II:

$$W\text{-}\psi\text{-}A\text{-}Z \qquad \qquad II$$

wherein A is a group selected to have affinity for the specificity pocket of a serine protease, especially a trypsin-like protease, W is a moiety selected to have affinity for a binding subsite of a serine protease, especially a trypsin-like protease, $\psi$ is a linker between W and A other than a natural peptide group or an N-substituted natural peptide group and Z is a C-terminal carboxy group or a replacement therefor.

As used herein, "natural" amino acid means an L-amino acid (or a residue thereof) selected from the group consisting of Ala=alanine
Arg=arginine
Asn=asparagine
Asp=aspartic acid
Cys=cysteine
Gln=glutamine
Glu=glutamic acid
Gly=glycine
His=histidine
Ileu=isoleucine
Leu=leucine
Lys=lysine
Met=methionine
Phe=phenylalanine
Pro=proline
Ser=serine
Thr=threonine
Trp=tryptophan
Tyr=tyrosine
Val=valine By "unnatural" amino acid is meant any α-amino acid (or residue thereof) other than the natural amino acids listed above. Unnatural amino acids therefore include the D-isomers of the natural L-amino acids. Examples of unnatural amino acids include for instance: D-Phe, norleucine, hydroxyproline, α-carboxyglutamic acid, pyroglutamic acid, and other amino acids having side chain protecting groups and which are capable of incorporation into the peptides of the invention, Where prefixed by "D" or "L", the foregoing names or abbreviations indicate an amino acid of D- or L-configuration respectively. A "D.L-" prefix indicates a racemic mixture of amino acids of the two configurations. Where no prefix is included, this means that the amino acid can be of either the D- or the L-configuration, except in the examples where residues are of L-configuration unless otherwise stated. For those groups of unspecified configuration in the text which can be of D or L configuration, L configuration is preferred.

Abbreviations and terms prefixed by "boro" indicate amino acids wherein the terminal carboxyl group —$CO_2H$ has been replaced by a group Z which is a boron functionality.

The term "analogue" when used in reference to amino acid residues or other moieties denotes an alternative to another group without implying that analogous groups impart the same properties to a compound. To the contrary, biological properties of compounds can be significantly chanced by replacing a moiety with an analogue thereof.

Where asymmetric centres in formulae herein are marked with an asterisk (*), this denotes a stereo configuration of either D or L.

Further symbols and abbreviations used herein have the following meanings:
Aa=amino acid
$Aa^p$=phosphonic acid analogue of Aa
Ac=acetyl
adal=adamantylalanine
Adgly=1-adamantylglycine
Apa=amidinophenylalanine
ArgCN=Arg, where COOH is replaced by CN
Baa=NH—CH—($CH_2CH_2CH_2Br$)B—
Boc=t-butyloxycarbonyl
BoroArg=NH—CH—[$CH_2CH_2CH_2NHC(NH)NH_2$]B
BoroHArg=NH—CH—($CH_2CH_2CH_2CH_2NHC(NH)NH_2$)B
BoroHpg=borohydroxypropylglycine
$COCH_2$boroHpg=—$COCH_2$—$CH(CH_2CH_2CH_2OH)$B
BoroLys=NH—CH—($CH_2CH_2CH_2CH_2NH_2$)B
BoroOrn=NH—CH—($CH_2CH_2CH_2NH_2$)B
BoroPro=analogue of proline in which the —COOH group is replaced by $BO_2Pin$
BPoc=biphenyl methyl oxycarbonyl
Bu=butyl
Bz=benzoyl
Bzl=benzyl
Cbz=benzyloxycarbonyl
Cha=cyclohexylalanine
Chg=cyclohexylglycine
Dba=α-phenylethylphenylalanine
DBU=diaza-bicycloundecane
DCC=dicyclohexylcarbodiimide
DCM=dichloromethane
DCU=dicyclohexylurea
DIEA=diisopropylethylamine
DMAP=4-dimethylaminopyridine
Dpa=β,β-diphenylalanine
Dtt=dithiothreitol
ESMS=electrospray mass spectrometry
Etg=α-ethylglycine
EtOAc=ethyl acetate
EtOH=ethylalcohol
Fgl=α-fluorenylglycine
Gpa=guanidinophenylalanine
HOBT=Hydroxybenzotriazole
Irg=isothiouronium analogue of Arg
-k-=amide bond replaced by CO—$CH_2$
LDA=lithium diisopropyl amide
Mbg=2-(2-methylbutyl)glycine Mpg=3-methoxypropylglycine
MCA=4-methyl-coumaryl-7-amide
MeOH=methylalcohol
MeOSuc=methoxysuccinyl
Mtr=4-methoxy-2,3,6-trimethylbenzenesulphonyl
Nal=naphthylalanine
$NASO_2$=napthylsulfonyl
NMR=nuclear magnetic resonance
Np=p-nitrophenyl
ONSu=N-hydroxysuccinimide
OPin=pinanediol
OPinac=pinacol
PfpOH=pentafluorophenol
Phg=phenylglycine
Pgl=pentylglycine
pip=piperidide
Pmc=2,2,5,7,8-pentamethylchroman-6-sulphate
Pms=phenyllactic acid
pNA=p-nitroanilide
Pyro=pyro-glutamic acid
p-OH-Me-Phal=p-hydroxymethylphenylalanine
p-TBDPS-O-Me=p-tertbutyldiphenylsilyloxymethyl-phenylalanine
rmm=relative molecular mass
TEA=triethylamine
THF=tetrahydrofuran
Thi=thiazolidinecarboxylic acid
Tiq=tetrahydroisoquinoline-3-carboxylic acid
TLC=thin layer chromatography
TMSal=trimethylsilylalanine
WSC=water soluble carbodiimide The term "aryl" as used herein includes aryl groups containing heteroatoms, i.e. heteroaryl groups.

The term "alkyl" includes cycloalkyl and alkyl containing cycloalkyl, where cycloalkyl is in particular cyclohexyl or cyclopentyl.

As used herein, "amino protecting group" means any amino protecting group employable in peptide synthesis. Examples include: alkyl (especially methyl or other $C_1$–$C_6$ alkyl), acetyl, benzoyl, BPoc, formyl, morpholinocarbonyl, trifluoroacetyl, methoxysuccinyl, aromatic urethane protecting groups such as benzyloxycarbonyl, aliphatic urethane protecting groups such as tertbutyloxycarbonyl or adamantyloxycarbonyl. Amino protecting groups are described in Gross and Meinhoffer, eds., The Peptides, Vol. 3, 3–88, and exemplified in D. W. Greene, "Protecting Groups in Organic Synthesis".

Preferred amino protecting groups include: $R^{10}(CH_2)_cOCO$— or $R^{10}(CH_2)_eSO_2$—, where $R^{10}$ is a $C_5$–$C_2$, preferably $C_6$–$C_{10}$, aryl, arylalkyl or alkylaryl group optionally substituted by halogen or —OH, especially phenyl, naphthyl or $C_1$–$C_4$ alkylphenyl, and e is 0 to 3.

In compounds of the invention having side chain amino groups, e.g. where $aa^1$, $aa^2$, $aa^3$ or $aa^4$ is Lys or Arg, additional N-protecting groups are desirable in the compound structure during synthesis. These protecting groups are optionally removed or exchanged in the final structure. For example Mtr (4-methoxy-2,3,6-trimethyl-benzenesulphonyl) or Pmc (2,2,5,7,8-pentamethylchroman-6-sulphate) may be used to protect Arg and Dtt (dithiothreitol) to protect Lys.

Similarly amino acid residues having acidic or hydroxy side chains may be suitably protected in the form of t-butyl, benzyl or other suitable esters or ethers, as is known in the art (e.g. Sheppard—"Solid Phase Peptide Synthesis, E. Atherton, R. C. Sheppard, IRL Press, Oxford, 1989).

Besides the true acid forms of the peptides of the above formula (1), within the scope of the present invention are also physiologically acceptable salts thereof. Preferred salts include acid addition salts, e.g., salts of benzene sulphonic acid (BSA), hydrochloric acid (HCl) hydrobromic acid (HBr), acetic acid, trifluoroacetic acid (TFA), succinic acid, citric acid and other addition salt-forming acids known in the art.

Within the scope of the present invention are peptides (or, more precisely, peptide analogues) which are modified by, in particular, isosteric replacement of one or more remaining peptide bonds by —CO—$CH_2$—, —CH(OH)—$CH_2$ or —$CH_2$—NH— linkages, or by $N_4$. The peptides may be in the free form or in a form protected at one or more remaining functional groups, e.g., amino, imino or amide (including peptide), nitro, carboxyl, hydroxyl, guanidino or nitrile. Examples of, and synthetic routes to, such further modifications of peptides are disclosed in for example EP-A-0118280 and corresponding U.S. Pat. Nos. 4,638,047 and 4,772,686, the disclosures of both of which references are incorporated herein by references, as well as in WO 92/07869.

The present invention has been shown to comprise peptides which exhibit good, and in many cases excellent, inhibitory properties with respect to a variety of serine proteases. Such enzymes include trypsin-like enzymes such as thrombin. Factor Xa and Factor VIIa, and chymotrypsin-like enzymes such as elastase.

The inventive compounds will now be considered in more detail. Unless otherwise stated, preferred features in the following description apply in particular to thrombin inhibitors, The C-Terminal Group (Z)

The moiety on the C-terminal side of the P1 residue (groups Z of formulae I and II) is not critical to the invention. It is a moiety which interacts with the active site triad residues (Asp-His-Ser) of a serine protease. Topically, the P1 residue is linked on its C-terminal side to a functional group which may be a carboxyl group (—COOH) or a derivative thereof, such as an ester, an amide or a ketone, for example, or even a nitrile group, Usually, Z does not comprise a peptide linkage, or a replacement therefor ($\psi$), to a $P1^1$ amino acid residue. More preferably the natural carboxy group is replaced by a heteroatom acid group, of which the preferred examples are boron or phosphorus acid groups, notably boronic acid residues [—$B(OH)_2$], phosphonic acid residues [—$P(O)(OH)_2$], phosphorous acid residues [—$P(OH_2)$] or phosphinic acid residues [—$P(O)(OH)(H)$].

A less preferred heteroatom acid group is sulphonyl [—$S(O)_2OH$].

In place of a heteroatom acid group there may be used a derivative thereof. The invention is not primarily concerned with selection of derivatives of the carboxy or heteroatom acid groups: in principle, any derivative group may be used which does not prevent the inhibiting function of the compound. Substituent groups include inert organic groups, generally containing a total number of carbon atoms and heteroatoms not exceeding 20. Representative inert groups are hydrocarbyl, optionally containing an ether or ester linkage and/or substituted by halogen or —OH.

In one class of embodiments, the acid derivatives have the hydrogen of an —OH group replaced by a substituent group, which may be linked to the oxygen by a functional group, for example a carbonyl or amino group. Preferred substituents are diol residues, as further described below.

In another class of embodiments an —OH group is replaced by an amino group, which may be mono- or di-substituted. An alternative replacement functional group is thiol, especially substituted thiol.

In other classes of compounds, an —OH group is replaced by an inert organic group (e.g. a hydrocarbyl group as described above) or by a halogen atom, especially fluorine.

One class of compounds has a C-terminal group (Z of formula I or II of the formula III:

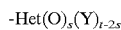
-Het(O)$_s$(Y)$_{t-2s}$     III wherein

Het is a heteroatom;

s is 0, 1 or 2;

t is the valency of Het, t-2s being an integer of at least 1, and each Y is independently hydrogen, halogen, hydroxy, substituted hydroxy, substituted thiol, amino or substituted amino, wherein two hydroxy groups, two thiol groups or an amino group are/is optionally substituted by a single divalent substituent.

Het is preferably boron or phosphorus, and most preferably boron.

Preferably, each Y is independently F or other halogen, $O\Sigma^1$ or $N\Sigma^1\Sigma^2$, wherein $\Sigma^1$ and $\Sigma^2$ are independently selected from H, hydrocarbyl and hydrocarbylcarbonyl, the hydrocarbyl groups optionally being substituted by one or more moieties selected from halogen, —OH or alkoxy and/or containing an ether or ester linkage (—O— or —COO—), which groups contain up to 20 carbon atoms, or wherein two Y groups taken together form the residue of a diol or a dithiol.

Particularly preferred C-terminal groups are of the formula

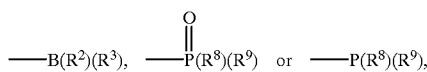

wherein:

$R^2$ and $R^3$ are each independently selected from halogen, —OH, —OR$^4$ and —NR$^4$R$^5$, where R$^4$ and R$^5$ are each independently a group of the formula R$^6$(CO)$_u$—, wherein u is 0 or 1, R$^6$ is H or an optionally halogenated alkyl, aryl or arylalkyl group containing up to (10-u) carbon atoms and optionally substituted by one or more groups selected from —OH, R$^7$(CO)$_v$O— and R$^7$(CO)$_v$—, wherein v is 0 or 1. R$^7$ is $C_1$–$C_{6-v}$ alkyl, or is an aryl, alkylaryl, arylalkyl or alkylarylalkyl group containing up to (10-v) carbon atoms.

or $R^2$ and $R^3$ taken together represent a residue of a diol or a dithiol;

$R^7$ and $R^8$ and are each independently selected from the group consisting of $R^2$, $R^3$, $R^4$ and $R^5$; and $R^9$ is a group selected from the following: —H, —OR$^4$, —OR$^5$.

One or both of $R^2$ and $R^3$ are preferably —OR$^4$ in which $R^4$ is preferably a said optionally halogenated alkyl, aryl or arylalkyl group optionally substituted as aforesaid.

Where the compounds have a C-terminal acid group substituted by the residue of a diol or dithiol, the diol or dithiol preferably comprises two or more —OH or, as the case may be, —SH groups connected by at least two connecting atoms. The connecting atoms are preferably in an organic moiety containing up to 20 and, more preferably, up to 10 carbon atoms.

The organic moiety may be a hydrocarbyl group optionally containing between the members of one or two pairs of adjacent carbon atoms an N, S or O atom. The organic moiety may be inertly substituted. Normally the substituted compounds are mono- or di- substituted, exemplary substituents being halogen especially —F, and —OH.

Preferred diol residues are of pinanediol, pinacol, perfluoropinacol, ethylene glycol, diethylene glycol, catechol, 1,2-cyclohexanediol, 1,2-cyclohexaneethanediol, 1,3-propanediol, 2,3-butanediol, 1,2-butanediol, 1,4-butanediol, 2,3-dimethylbutane-2-3-diol, glycerol, or diethanolamine or another amino dihydroxy alcohol. Of these, pinanediol and especially pinacol are most preferred. The most preferred compounds comprise a boronic acid residue substituted with a diol residue.

As described in more detail hereafter, the C-terminal acid group may be bonded to an anion-binding exosite association moiety through an 18Å–42Å linker group.

The Replacement Non-Amide Bond (ψ)

The compounds of the invention are all characterised in that a natural peptide linkage (—NHCO—) is replaced by an alternative linker group. The replaced peptide link is defined as the P2-P1 link in the first aspect of the invention and represented by ψ in formulae I and II. For convenience, the symbol ψ will hereafter be used.

ψ is a group which may be included in a compound of the invention without the inhibiting activity of the compound being lost. Preferred ψ groups enhance the inhibitory activity of the compound. If ψ is long, there is a tendency for binding of the peptide inhibitor to the target enzyme to be weakened. Typically, therefore, ψ has a chain length of no more than 5 atoms, i.e. no more than 5 atoms separate the carbon atoms of the residues linked by ψ. More preferred ψ groups have a chain length of 2 or 3 atoms, a chain length of two atoms being most preferred.

ψ is preferably not isoelectronic with —NHCO— . One less preferred class of embodiments does not have ψ groups of the so-called isosteric (to —CONH—) type, such as —COCH$_2$—, —CH(OH)—CH$_2$—, —CH$_2$—NX— or —NHCO—, for example. However, —COCH$_2$— and —CH(OH)—CH$_2$— are very acceptable in some compounds. Representative ψ groups include —CO$_2$—, —CH$_2$O—, —NHCO—, —CHYCH$_2$—, —CH=CH—CO(CH$_2$)$_p$CO— where p is 1, 2 or 3, —COCHY—, —CO$_2$—CH$_2$NH—, —CHY—NX—, —N(X)CH$_2$—N(X)CO—, —CH=C(CN)CO—, —CH(OH)—NH—, —CH(CN)—NH—, —CH(OH)—CH$_2$ or —NH—CHOH—, where X is H, an amino protecting group (e.g. CH$_3$) and Y is H or halogen (especially F). Exemplary Y-containing groups are —CH$_2$CH$_2$—, —COCHF— and —CH$_2$NX—. The most preferred ψ groups are —CO$_2$— and —CH$_2$O—.

The N-terminal Group (X)

The N-terminal group (X of Formula I) may be hydrogen (to form an —NH$_2$ group) or an amino protecting group. The amino protecting group of the pharmaceutical compounds may be any pharmaceutically acceptable group, for example as described hereinbefore. Alkyl groups, e.g. $C_{1-C6}$ alkyl such as methyl, for example, are suitable. A preferred class of protecting groups are those of the formula R$^{10}$(CH$_2$)$_e$OCO— and R$^{10}$(CH$_2$)$_e$SO$_2$—, wherein e is 0, 1, 2 or 3 and R$^{10}$ is a $C_5$–$C_{12}$ aryl, $C_5$–$C_{12}$ arylalkyl or $C_5$–$C_{12}$ alkylaryl group optionally substituted by halogen (e.g. —F or —Cl) or —OH: such protecting groups are especially preferred when m and n of Formula I are both 0, and are described in more detail hereafter in relation to compounds in which m and n are both 0 under the heading "The Amino Acid Sequence". Particularly preferred R$^{10}$ groups when m and n are 0, or when m is 0 and n is 1, are phenyl, naphthyl, $C_1$–$C_4$ alkylphenyl or phenyl $C_1$–$C_4$ alkyl. In preferred embodiments, e is 0.

Selection of N-terminal groups can enhance bioavailability of active compounds, although not necessarily effecting potency against the isolated target enzyme. Typical groups of the active compounds include morpholin-N-alkyl or N-carbonyl derivatives, succinimidyl, alkyl or aryl-alkyl-sulphonyl, N-methylpiperazine or groups as known in the art, such as Rosenberg, et al. *J.Med.Chem.*, 1993, 36, 449–459 or Hashimoto, N. et al. *Pharm.Res.*, 1994, 11, 1443–1451, or Bernstein, P. R., et al. *J.Med.Chem.*, 1994, 37, 3313–3326. These groups can be introduced to the peptides by hydrogenation to remove urethane protecting groups used for synthesis to give the free amino terminus (see Example 2) and reacylation or acetylation with a derivative of the appropriate X group.

Introduction of N-methyl groups can improve in-vivo activity as is known in the art, Hashimoto, N. et al *Pharm.Res.*, 1994, 11, 1443–1451.

The Amino Acid Sequence

Peptide serine protease inhibitors comprise a sequence of amino acid residues and are commonly tripeptides. The specific sequence is not critical to the invention. The amino acids may be natural or unnatural, e.g. the D-isomer or racemate of a natural amino acid; they may be modified amino acids in which the α-H is replaced by a substituent, for example hydrophobic or hydrophilic groups containing up to about 20 or even more, e.g. 22, carbon atoms. More preferred substituents contain up to 15, or preferably up to 10, carbon atoms Preferred classes of replacements for the α-hydrogen of the amino acid residues are:

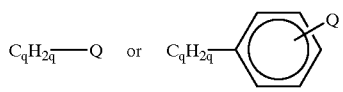
(i)

where Q=amino, amidino, imidazole, guanidino, $N_3$, or isothioureido, and q is an integer of from 1 to 5;

(ii) a side chain of a natural amino acid other than glycine; or (iii) a moiety (other than hydrogen) of the formula V or VI:

$$—(CO)_a—(CH_2)_b—D_c—(CH_2)_d—E \qquad V$$

$$—(CO)_a—(CH_2)_b—D_c—(CH)_e(E^1)(E^2) \qquad VI$$

wherein:

a is 0 or 1;

e is 1;

b and d are independently 0 or an integer such that (b+d) is from 0 to 4 and (b-e) is from 1 to 4;

c is 0 or 1;

D is O or S;

E is H, $C_1$–$C_6$ alkyl, or a saturated or unsaturated cyclic group which normally contains up to 14 members and preferably is a 5–6 membered ring or an 8–14 membered fused ring system, which alkyl or cyclic group is optionally substituted by up to 3 groups (e.g. 1 group) independently selected from —$R^{13}$, —$R^1OR^{13}$, —$R^1COR^{13}$, —$R^1CO_2R^{13}$, —$R^1O_2CR^{13}$, nitro and cyano, wherein $R^1$ is —$(CH_2)_f$ and $R^{13}$ is —$(CH_2)_gH$ or a moiety which has a total number of carbon and heteroatoms from 5 to 10 and which contains a ring system (e.g. an aryl group) and optionally an alkyl and/or alkylene group, wherein f and g are each independently from 0 to 10, g preferably being at least 1 except that —OH is a preferred substituent, provided that (f+g) does not exceed 10, preferably does not exceed 6 and more preferably is 1, 2, 3 or 4, and provided that there is only a single substituent if the substituent is a said moiety containing a ring system, or E is $C_1$–$C_6$ trialkylsilyl; and $E^1$ and $E^2$ are each independently a 5 or 6 membered ring;

in which moiety of Formula V or VI any one or more hydrogen atoms bonded to a carbon atom is optionally replaced by halogen, especially F.

Certain classes of compounds falling within definition (iii) above are preferred. Preferably a is 0. If a is 1, c is preferably 0. Preferably, (a+b+c+d) and (a+b+c+e) are no more than 4 and are more preferably 1, 2 or 3. (a+b+c+d) may be 0.

Exemplary groups for E, $E^1$ and $E^2$ include aromatic rings such as phenyl, naphthyl, pyridyl, quinolinyl and furanyl, for example; non-aromatic unsaturated rings, for example cyclohexenyl: saturated rings such as cyclohexyl, for example; and fused ring systems containing both aromatic and non-aromatic rings, for example fluorenyl. A preferred class of E, $E_1$ and $E^2$ groups are aromatic rings, especially 6- membered aromatic rings. $E^1$ and $E^2$ are preferably phenyl. The phenyl or other aryl groups may be substituted by nitro or cyano, preferably at the 4-position.

In one class of embodiments, E contains a substituent which is $C_1$–$C_6$ alkyl, ($C_1$–$C_5$ alkyl)carbonyl, carboxy $C_1$–$C_5$ alkyl, aryl, especially 5-membered or preferably 6-membered aryl (e.g. phenyl or pyridyl), or arylalkyl (e.g. arylmethyl or arylethyl where aryl is preferably 6-membered).

In another class of embodiments, E contains a substituent which is $OR^{13}$, wherein $R^{13}$ preferably is a 6-membered ring, which may be aromatic (e.g. phenyl) or non-aromatic (e.g. morpholine or piperazine) or is alkyl (e.g. methyl or ethyl) substituted by such a 6-membered ring.

A particularly preferred class of moieties of formula V or VI are those in which E is a 6-membered aromatic ring substituted, preferably at the 2-position or 4-position, by —$R^{13}$ or —$OR^{13}$.

A further preferred class of substituents of formula V or VI are of the formula $C_qH_{2q}T$ or

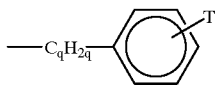

wherein q is as defined above and T is hydrogen, halogen (e.g. F), —$SiMe_3$, —$R^{13}$, —$COR^{13}$, $CO_2R^{13}$, —$O_2CR^{13}$ or a moiety which has a total number of heteroatoms from 5 to 10 and which contains a ring system, especially an aryl group, and optionally an alkyl residue or an alkylene residue, or both. Said moiety is preferably 5-membered or more preferably 6-membered aryl (e.g. phenyl or pyridyl) or arylalkyl (e.g. arylmethyl or arylethyl) where aryl has 5 or preferably 6 members. In preferred embodiments T is at the 2-position of the phenyl group and is —$R^{13}$, —$COR^{13}$, —$CO_2R^{13}$ or —$O_2CR^{13}$, and $R^{13}$ is $C_1$–$C_{10}$ alkyl and more preferably $C_1$–$C_6$ alkyl.

A class of residues which includes certain natural amino acid residues as well as many unnatural amino acid residues is of the formula

—HNC($W^1$)($W^2$)CO— wherein $W^1$ and $W^2$ may be the same or different and are selected from hydrogen and hydrogen replacement groups (i), (ii) and (iii) described above in relation to amino acid residues in which the α-hydrogen is replaced by a substituent; preferably, one of $W^1$ and $W^2$ is hydrogen. In other residues of this formula, $W^1$ and $W^2$ together with the carbon atom to which they are bonded form a ring system, especially a hydrophobic ring system such as cycloalkyl (e.g. $C_3$–$C_7$ cycloalkyl) or $W^1$ and $W^2$ together form an alkenyl or aralkenyl group, e.g. PhCH=, Alternatively, —HNC($W^1$)($W^2$)CO— is the residue of an amino acid in which $W^1$ is H and W is a group which together with the α-amino group forms a cyclic group, i.e. the amino acid is of the formula IX:

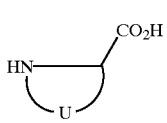

IX herein U is a moiety forming a cyclic structure, which may be substituted or unsubstituted. The cyclic structure is preferably a 4–6 membered ring or an 8–10 membered fused ring system optionally substituted by up to 3 groups independently selected from —$R^{13}$, —$R^1OR^{13}$, —$R^1COR^{13}$, —$R^1CO_2R^{13}$ and —$R^1O_2CR^{13}$, wherein $R^1$ and $R^{13}$ are as hereinbefore defined. Exemplary substituents are $C_1$–$C_3$ alkyl. Any one or more hydrogen atoms bonded to a carbon atom may optionally be replaced by halogen, especially F.

The cyclic structure may contain additional heteroatoms, for example sulphur, such as in a 5- or 6-member ring, for example. A ring carbon atom may be a member of a carbonyl group, for example as part of an amide linkage in the cyclic structure, as in pyroglutamic acid, for example. In one preferred class of compounds the cyclic structure preferably contains no heteroatom in addition to the α-amino nitrogen. In fused ring structures, the ring fused to that containing the α-amino nitrogen is preferably aromatic and most preferably phenyl, as in D-Tiq.

WO 92/07869 and EP 0118280 disclose peptide inhibitors in which a P1 residue which is Arg or an Arg analogue is linked through a ψ linkage to $P1^1$ residue which is exemplified as Gly but may also be an amino acid residue with an optionally hydroxylated hydrocarbon side chain. One class of compounds have a structure falling within formula I in which $aa^1$ is not glycine. When $aa^1$ is glycine ($W^1$=$W^2$=H), then $aa^2$ is preferably Phe or a Phe analogue (i.e. $aa^3$ $aa^2$ is a sequence favoured by Kallikrein); in any event, in those compounds of this structure where $aa^1$ is glycine, $aa^2$ is not arginine, 3-($4^1$-amidinophenyl)-alanine or Gpa and normally is not any other amino acid whose side chain has a terminal amidino group, and more preferably is not any other arginine analogue as defined below.

The number of $aa^4$ residues is not critical to the invention but in preferred embodiments m is from 0 to 7 and more usually 0 to 5, e.g. 0, 1 or 2 especially 0. Normally there is an $aa^3$ residue (i.e. n=1) but if X is a suitable group m and n may both be zero. As described further below, the invention also contemplates monopeptides of the formula X-ψ-$aa^1$.

The serine proteases are a widely studied family of enzymes, and a considerable body of knowledge exists as to amino acid sequences preferred by different enzymes. The coagulation proteases are trypsin-like enzymes which in nature favour Arg, Lys or similar residues at P1. An important factor for thrombin selectivity is the choice of P1 residue, for example by choosing methoxyalkyl as P1 residue. Thrombin exhibits a preference for hydrophobic P2–P4 residues and, in the case of tripeptides favours D-configuration at P3. Thrombin best accommodates inhibitors containing a P4 residue in which both the P3 and P4 residues are hydrophobic amino acids of L-configuration. Particularly favoured (P4)P3P2 residues for some serine proteases are as follows:

Thrombin: D-PhePro

Kallikrein: ProPhe

Elastase: AlaPro

Factor X: IleuGluGly

Factor VIIa: L-PhePhe

Plasmin: GluPhe

Urokinase: PhePro

Elastase is a chymotrypsin-like serine protease and favours phenylalanine and alanine and like (hydrophobic) amino acid residues at P1. Plasmin and urokinase are trypsin-like.

In alternative favoured sequences the above amino acid residues may be replaced by analogue residues. Preferred analogous residues of amino acids include those sharing the same polarity or charge.

Residues analogous to Lys or Arg and amongst the residues favoured by trypsin-like proteases at P1 are those with group (i) side chains and an α-hydrogen, that is, residues of the formula

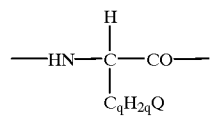

and

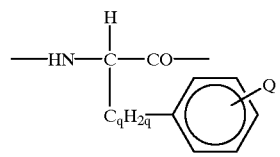

in which Q includes amino, amidino, imidazole, guanidino, $N_3$ or isothioureido. Specific analogy residues to Lys and Arg include Gpa, amidinoPgl or amidinopiperidylglycine. Also very acceptable P1 residues for the trypsin-like proteases are those with hydrophobic side chains, including Phe and its analogues.

Suitable hydrophobic side chains for the P1 residue include group (iii) side chains of Formula V. especially those in which a is 0, D is O or is absent and/or E is H, $C_1$–$C_6$ alkyl, $C_1$–$C_6$ trialkylsilyl or $C_6$–$C_{10}$ aryl optionally substituted by up to three groups selected from $C_1$–$C_4$ alkyl, halogen and $C_1$–$C_4$ alkoxy, of which H is less preferred. Preferably there is one said substituent; preferably the Formula V groups contain a total number of carbon atoms and heteroatoms not exceeding 14, more preferably not exceeding 10 and most preferably not exceeding 8.

It will therefore be seen that, as suitable P1 residues for inhibitors of trypsin like proteases, there may be mentioned groups of the formula

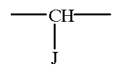

wherein

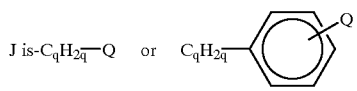

where Q and q are as defined above or is a group of the formula

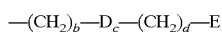

wherein:
b, d, c and e are as defined above;
D is 0; and
E is H, $C_1$–$C_6$ alkyl, $C_1$–$C_6$ trialkylsilyl or $C_6$–$C_{10}$ aryl optionally substituted by one or, less preferably, two or three groups selected from $C_1$–$C_4$ alkyl, halogen and $C_1$–$C_4$ alkoxy. $C_1$–$C_6$haloalkyl is a preferred E group.

Particularly preferred hydrophobic P1 side chains are $C_1$–$C_8$, preferably $C_1$–$C_6$, alkyl (e.g. ethyl, isopropyl, pentyl), alkoxyalkyl containing from 2 to 6 carbon atoms (e.g. methoxypropyl) and moieties containing a 5–10 membered aryl or heteroaryl group and optionally a total number of alkyl and/or alkylene carbon atoms not exceeding 4, especially phenyl $C_1$–$C_4$ alkyl (e.g. phenylmethyl). Any of the aforesaid alkyl or alkylene groups may be substituted by one, or more than one, halo atom, e.g. fluoro or bromo; thus bromopropyl, especially 3-bromopropyl, or other bromoalkyl (usually substituted by Br at the terminal carbon) is a preferred P1 side chain.

Methoxyalkyl is a particularly preferred side chain. In some embodiments the P1 side chain is $C_1$–$C_6$ hydroxyalkyl, 3-methoxypropyl, 3-halopropyl and 3-hydroxypropyl and alkyl homologues thereof are particularly preferred.

Especially for inhibitors of trypsin-like enzymes, e.g. thrombin, W of formula II normally comprises a sequence of up to 9 amino acids, and more usually of up to 7 amino acids, wherein at least one amino acid has a hydrophobic side chain, e.g. Phe or a Phe analogue. For thrombin inhibitors the P3 ($aa^3$) residue is desirably hydrophobic: the P2 residue ($aa^2$) is also preferably hydrophobic and more preferably is Pro or a ring homologue thereof. Any P4 residue of a thrombin inhibitor is preferably also hydrophobic.

Residues analogous to Phe include those with group (iii) side chains and those of formula IX and those in which $W^1$ and W2 together form a hydrophobic ring system or an alkenyl or aralkenyl group. A class of Phe analogues with group (iii) side chains or of formula IX. which class is in particular preferred for the P2 and especially P3 residues, comprises compounds of the Formula VII:

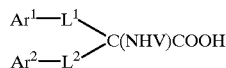

wherein $Ar^1$ and Ar2 are each independently selected from the group consisting of H; phenyl; phenyl substituted by halogen (e.g. p-halophenyl, especially p-iodophenyl), a $C_1$–$C_6$ group which is alkyl or alkyl substituted or interrupted by a carbonyl or carbonyloxy group (e.g. alkylcarbonyl or alkoxycarbonyl) or substituted by —$R^{14}$ or —$OR^{14}$ wherein $R^{14}$ is a 5- or 6-membered aromatic or non-aromatic ring or is $C_1$–$C_4$ alkyl substituted by such a 6-membered ring; bipyridyl; furanyl; chromanyl; quinolinyl; thienyl; pyridyl; α- or β-naphthyl; thionaphthyl; indolyl; p-iodophenylalanyl; diphenyl-methyl; or fluorenyl; or are wholly or partially saturated groups corresponding to any of these (e.g. cyclohexyl, piperidyl or tetrahydroisoquinolyl); $Me_3Si$, or 2.2.2-trichloroethyl. Any of the foregoing groups is optionally substituted by up to three groups selected from $C_1$–$C_3$ alkyl, $C_1$–$C_3$ alkoxy, $R^{13a}CO$— wherein $R^{13a}$ is H. $CH_3$ or $C_2H_5$, $R^{13a}OR^{1a}$— or $R^{13a}COR^{1a}$—, wherein $R^{1a}$ is —$CH_2$—, —$C_2H_4$— or —$C_3H_6$—.

$L_1$ and $L_2$ are each independently selected from the group consisting of $CH_2$, $CH_2$—$CH_2$, O—$CH_2$, S—$CH_2$, and a bond.

V is H, or —NHV and one of $Ar^1$—$L^1$ and $Ar^2$—$L^2$ together form a group of the formula

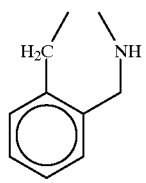

It is preferred that, if $L^1$ or $L^2$ is a single bond, its attached Ar group be diphenylmethyl, fluorenyl or cyclohexyl.

Preferably, $Ar^2L^2$ is H.

Particularly preferred Phe analogues for the P3 residue are D-Phe substituted at the phenyl 2-position (i) by a $C_1$–$C_6$ group which is alkyl or alkyl substituted or interrupted by a carbonyl or carbonyloxy group (e.g. is alkylcarbonyl or alkyloxycarbonyl) or (ii) by a 5 or 6 membered aryl group; D-Dpa; Dba: Pms; α- or βNal; TMSal; Chg; Phg; D-Tiq or a para ether of D-Tyr. An exemplary substituted phenylalanine residue is D-phenylalanine-2-carboxylic acid methyl ester.

Exemplary tyrosine-para-ethers are D-tyrosine-O-phenyl, D-tyrosine-O-ethyl-2-(N-morpholine) and D-tyrosine-O-ethyl-2-N(piperazine). The most preferred Phe analogues are Dpa. Nal and Dba. Other preferred Phe analogues for in particular the P3 residue have side chain c). d), e) f), g), or h) of U.S. Pat. No. 5,288,707 and EP 0471651.

As a modification of tripeptides in which the P3 residue is in particular Phe or another hydrophobic residue (e.g. Mpg), there may be used a dipeptide (m and n=0 in Formula I) in which X is of the formula $R^{10}(CH_2)_eCOO$— or $R^{10}(CH_2)_eSO_2$—wherein $R^{10}$ is a $C_5$–$C_{12}$ aryl, $C_5$–$C_{12}$ arylalkyl or $C_5$–$C_{12}$ alkylaryl group optionally substituted by halogen or —OH and e is 0 to 3. As another contemplated modification the compounds of the invention may take the form of monopeptides of the formula X-ψ-$aa^1$, wherein X is $R^{10}(CH_2)_eCOO$— or $R^{10}(CH_2)_eSO_2$— and $aa^1$ is suitably a hydrophobic residue. Particularly preferred $R^{10}$ groups are $C_9$–$C_{10}$ fused ring systems containing a phenyl ring, especially naphthyl. Where $R^{10}$ is a fused ring system, e is preferably 0; if $R^{10}$ is a single ring, e may suitably be 1. In those compounds in which $R^{10}$ is a fused ring system, the residue of the acid function —COO— or —$SO_2$— is preferably —$SO_2$—. Particularly preferred amino protecting group analogues for Phe are benzyloxycarbonyl (Cbz) and naphthylsulfonyl.

Residues analogous to proline are preferably those ring homologues included in the formula VIII

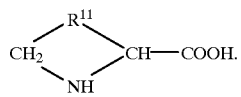

VIII or its $C_1$–$C_3$ alkyl substituted derivatives, where $R^{11}$=— $CH_2$—, —$CH_2$—$CH_2$—, —S—$CH_2$—, —S—$C(CH_3)_2$— or —$CH_2$—$CH_2$—$CH_2$—. Up to 3 $C_1$–$C_3$ alkyl groups, e.g. methyl, may substitute 1 or more carbon atoms. Normally any substituent is on a —$CH_2$— group. Normally a —$CH_2$— group is substituted by no more than 1 alkyl group.

[Formula VIII=proline when $R^{11}$=—$CH_2$—$CH_2$—].

Particularly preferred proline analogues are 2- and 3-thioproline and pipecolic acid. Inhibitors of thrombin, and certain other inhibitors as indicated below, preferably have proline at their P2 position. Kallikrein inhibitors preferably have proline at their P3 position. These proline residues may be replaced by proline analogues.

Those residues which are an analogue of Phe, Arg or Lys preferably have an α-hydrogen, but the hydrogen may be replaced by another group, e.g. a W moiety.

As already indicated, preferred classes of P1 residues of the inventive compounds are (i) Arg, Lys and their analogues, and (ii) hydrophobic residues. Particularly favoured (P4)P3P2 sequences for thrombin and six other enzymes are listed above; preferred inhibitors for these seven enzymes include those in which the (P4)P3P2 residues are the favoured ones or analogues thereof However, the most preferred inhibitors are not restricted to the favoured residues and their analogues, as will be revealed by a study of the following Table A which indicates the most preferred (P4)P3P2 residues for the seven enzymes.

TABLE A

| Enzyme | Residue Sequence |
|---|---|
| Thrombin | D-Phe-/substituted D-Phe-/D-Dpa-/Dba-/Pms-/α-Nal-/β-Nal-/TMSal-/Chg-/Phg-/D-Tiq-/para-ether of D-Tyr-/NaSO$_2$-Pro |
| Kallikrein | ProPhe |
| Elastase | AlaPro, LeuPro, AlaAla, LysLeu, GlyAla |
| Factor Xa | IleuGluGly, PyroGluGly, ArgGly, ChaGly |
| Factor VIIa | L-PhePhe, NalPhe, D-TiqPhe, NalThr, NalPhg |
| Plasmin | GlyPhe, IlePro |
| Urokinase | PhePro, GluGly |

It is especially desirable for inhibitors to include both a preferred P1 residue for the target enzyme and preferred subsite binding peptide sequences (e.g. P3P2) for the enzyme. For thrombin, tripeptide inhibitors are preferred, especially tripeptide boronates, and a particularly preferred sequence is PhePro-ψ-BoroMpg, especially inhibitors of the formula Cbz-D-PhePro-ψ(—$CO_2$— or —$CH_2O$—)BoroMpgOPin/Pinacol.

The P1 Mpg residue may be replaced by Pgl.

Residues may be in either D- or L-configuration. D-configuration is preferred for the P3 residue of thrombin inhibitors.

Variants

The essential feature of the inventive compounds is their possession of a replacement bond (ψ) for a natural peptide bond as defined. Other features of the compounds are not of the essence, provided that a compound inhibits its target enzyme.

The compounds of the invention may therefore be in the form of a pharmaceutically acceptable salt thereof and/or comprise one or more protectable functional groups (e.g. —OH or —$NH_2$) protected by a pharmaceutically acceptable protecting group. Suitable salts include acid addition salts, as described above, and those of acid groups with Group I or Group II metal cations (e.g. Na$^+$, K$^+$, Mg$^{2+}$, Ca$^{2+}$). As protecting groups of protectable functional groups, there may be mentioned t-butyl and benzyl as protecting groups for —OH and —COOH functions.

It is known in the art to replace other amide linkages than the P2-P 1 link with unnatural replacements, especially so-called isosteric/isoelectronic linkers. The invention encompasses peptides in which one or more amide linkages other than the P2-P1 linkage are also replaced by an unnatural linker ψ, e.g. a preferred ψ group of this invention or, more preferably, a so-called isosteric group, e.g. —$COCH_2$—, —CH(OH)—$CH_2$— or —$CH_2$—$NH_2$—. Such replacement of peptide bonds other than the P2-P1 bond is described, for example, in EP 0118280.

An additional or alternative modification is the inclusion in a thrombin inhibitor molecule of a thrombin anion exosite association moiety. It is known in the art to include a thrombin anion binding exosite association moiety (ABEAM) in thrombin. The ABEAM domain may comprise an) moiety which binds to the anion binding site of the target protease. Examples include amino acids 56–64 of hirudin, amino acids 1675–1686 of Factor V. amino acids 272–285 of platelet glycoprotein Ib, amino acids 415–428 of thrombomodulin, amino acids 245–259 of prothrombin Fragment 2 and amino acids 30 to 44 of fibrinogen Aα chain. In addition, the ABEAM component may be selected from any of the hirudin peptide analogues described by J. L. Krystenansky et al. "Development of MDL-28. 050. A small Stable Anththrombin Agent Based On A Functional Domain of the Leech Protein, Hirudin". *Thromb, Haemostas.*, 63. pp. 208–14 (1990).

Exemplary ABEAMS are described in WO 91/02750. (corresponding to U.S. Ser. Nos. 395,482 and 549,388) the disclosure of which is incorporated herein by reference. WO 91/02750 describes that the catalytic site-directed moiety of a thrombin inhibitor is linked to an ABEAM through a linker having a length of from 18 Å to 42 Å. The linker, which may be an amino acid sequence, is exemplified as bridging the C terminal of the catalytic site-directed moiety (CSDM) and the N-terminal of the ABEAM.

A representative ABEAM containing structure of the invention is:

D-PhePro-ψ-Arg-B(OH)-linker-ABEAM.

where LINKER may be 7-residue peptide.

The C-terminal boronic acid residue of the CSDM domain may be replaced by another heteroatom acid residue, e.g. a phosphonic acid residue.

Affinity Properties

The inhibitors compounds of the invention have affinity for one or more serine proteases. The serine protease may be chymotrypsin-like or, more preferably, trypsin-like. Exemplary enzymes are thrombin, kallikrein, elastase. Factor Xa. Factor VIIa, plasmin and urokinase. The most preferred enzymes have affinity for thrombin.

Compounds which have affinity for an enzyme significantly inhibit or retard the enzyme's activity. It is desirable for the compounds to have an inhibition constant (Ki) for a target enzyme of 0.5 μM or less, preferably of 0.3 μM or less and most preferably of 0.1 μM or less. In some cases a Ki of 0.05 μM or less is obtained, e.g. of about 0.035 to 0.04 μM (say, 0.039). The Ki values herein refer to values determined at 37° C.

It is often preferred for the inhibiting compounds to be selective towards one enzyme, e.g. to have a Ki for the selected enzyme of 0.1 μM or less (e.g. of between about 0.035 to 0.09 μM), and a Ki towards other serine proteases exceeding 0.1 μM and more preferably exceeding 0.2 μM, e.g. 0.25 μM or more. The Ki towards non-selected enzymes may exceed 0.5μM or 1 μM.

In one class of inhibitory compounds, the ratio of Ki for non selected enzymes: Ki for the selected enzyme is preferably at least 2 and more preferably at least 3. The Ki ratio may be at least 5.

A discussion of the inhibition constant Ki and a description of a method for determining it follows in the Examples.

Synthesis

The novel peptides of the present invention can be prepared by using, for example, generally known peptide synthesis methods. It is convenient in many instances to premake as intermediates the binding subsite affinity moiety $[X-(aa^4)_m-(aa^3)_n-(aa^2)$ of Formula I ]and the specificity pocket affinity moiety with its attached C-terminal group $[(aa^1)-Z$ of Formula I ]. The two intermediates contain suitable functional groups to react together to form the target non-natural amide bond [ψ of Formula I] and are caused or allowed to react together to form the compound (or a precursor thereof to undergo one or more further functional group transformations).

Thus the invention includes intermediates of the formula $X-(aa^4)_m-(aa^3)_n-(aa^2)-G^1$ or $W-G^1$ and $G^2-(aa^1)-Z$ or $G^2$-A-Z, wherein $G^1$ and $G^2$ are groups which may be reacted together to form a linking group other than a natural amide bond, optionally after "working up" (e.g. hydrogenation) of the direct product. In certain compounds of the invention. $G^1$ is not —COOH (and sometimes is not an ester or other reactive derivative thereof) and $G^2$ is $H_2N$—.

Exemplar $G^1$ and $G^2$ groups are as follows:

TABLE B

| ψ | $G^1$ | $G^2$ |
|---|---|---|
| —CO$_2$— | —COOH | leaving group, e.g. Cl, Br,I |
| —CH$_2$O— | —CH$_2$OH | Leaving group, e.g. Cl, Br, I |
| —COCH$_2$— | —COCH$_2$Br, or —COCH$_2$Boc | CHR-Z* Leaving group, e.g. Cl, Br, I |
| —CH(CN)NH— | —CHO | CHR-Z* |
| —CHOHCH$_2$— | —CHO | CHR-Z* |
| —CH=CH— | —NHCHRCH$_2$COH | (EtO)$_2$PO— |
| —CH$_2$—CH$_2$— | | make —CH=CH— then hydrogenate |
| —CH$_2$NH— | —CHO | H$_2$N— |

In Table B the symbol "R" designates the side chain of the P1 amino acid.
* = $G^2$-(aa$^1$)-Z Preferred intermediates of the invention are of the formula:

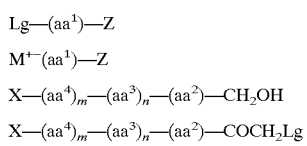

wherein Lg is a leaving group and M$^+$ is an alkali metal ion or another cation. Some representative syntheses of ψ linkages are described in more detail below:

ψ(CO$_2$):
Species where (aa$^2$) has a free carboxyl group (CO$_2$H), and $G^2$ is a leaving group, preferably a halogen, and the base DBU (Diazabicycloundecane) are used.

ψ(CH$_2$O):
Species (aa$^2$) which contain a free hydroxyl group (OH), and $G^2$ is a leaving group, especially halogen, e.g. Cl, Br and the base DBU or an organolithium (e.g. Butyl lithium) are used.

ψ(CH$_2$CH$_2$) where Z is —P(O)(R$^8$)(R$^9$) or —P(R$^8$)(R$^9$):
(aa$^2$) has a CH$_2$Hal G$^1$ group (Hal=halogen) and group $G^2$ is WCH$_2$Z, and a base such as NaH or BuLi is used.

ψ(CH$_2$N):
Species (aa$^2$) which has an aldehyde (CHO) G$^1$ group and $G^2$ is an amino group, and the reagent sodium cyanoborohydride are used.

ψ(COCH$_2$):
Ketomethylene bonds (COCH$_2$) can be prepared by reaction of a unit X-(aa$^4$)$_m$-(aa$^3$ )$_n$-(aa$^2$)-carbonyldimmidazole and the lithium salt of tert-butyl acetate to give a beta-diketone X-(aa$^4$)$_m$(aa$^3$)$_n$(aa$^2$)—COCH$_2$COOtBU, and alkylation with NaH and a halomethylketone (Hoffman, R. V. and Kim, H. O., Tet.Lett.,1992, 33, 3597–3582) or α-haloboronate (e.g. Hal—CHRBO$_2$Pin) or α-halophosphonate and subsequent hydrolysis.

Alternatively reaction of X-(aa$^4$)$_m$-(aa$^3$)$_n$-(aa$^2$) with diazomethane, then HBr gives the halomethylketone X-(aa$^4$)$_m$-(aa$^3$)$_n$-(aa$^2$)—COCH$_2$Br, this is then reacted with the carbanion of CH$_2$RBO$_2$Diol or RCH$_2$P(O)(OR')$_2$.

ψ[CH(CN)NH]:
Prepared by the method of Herranz, R., Suarez-Gea, M. L., Vinuesa, S., Garcia-Lopez, M. T. and Martinez, M., Tet.Let., 1991, 32, 7579–7582 or Suarez-Gea, M. L., Garcia-Lopez, M. T. and Herranz, R., J.Org.Chem., 1994, 59, 3600–3603: reaction of X-(aa$^4$)$_m$-(aa$^3$)$_n$-(aa$^2$)-CHO with trimethylsilylcyanide, ZnCl$_2$ and NH$_2$(aa$^1$)Z.

ψ(CHOHCH$_2$):
By the methods of Boyd, S. A., Mantei, R. A., Hsiao, C. N. and Baker. W. R., J.Org.Chem., 1991, 56, 438–442 or Kano, S., Yokomatsu, T. and Shibuya, S., Tet.Lett., 1991, 233–236: reaction of X-(aa$^4$)$_m$-(aa$^3$)$_n$-(aa$^2$)CHO with the carbanion of CH$_2$RBO$_2$ diol or CH$_2$RP(O)(OR')$_2$.

ψ(COCHF):
By reaction of an oxazolone with (CHR=CFCO)$_2$O, in a modification of the method as described by Hong, W., Dong, L., Cai. Z. and Titmas. R., Tet.Lett. 1992, 33, 741–744. Then hydroboron, possibly in the presence of Palladium catalyst, of the X-(aa$^4$)$_m$-(aa$^3$)$_n$-(aa$_2$)COCFCHRBO$_2$Diol.

ψ(CH$_2$=CH) and ψ(CH$_2$CH$_2$):
Reaction of X-(aa$^4$)$_n$(aa$^3$)$_n$NHCHRCH$_2$CO-H (as NH$_2$CHRCH$_2$COH is β-alaninol) and (EtO)$_2$PO—CHR—BO$_2$Diol with base (e.g. NaH), in a modification of the method of Rodriguez M., Heitz, A. and Martinez, J., Int.J.pep.Prot.res., 1992, 39, 273–277. This gives the unsaturated analogue ψ(CH=CH) of the form X-(aa$^4$)$_m$-(aa$^3$)$_n$NHCHR$^1$CH2CH=CHRBO$_2$Diol. This can be hydrogenated with palladium on charcoal to give X-(aa$^4$)$_m$-(aa$^3$)$_n$NHCHR$^1$—CH$_2$CH$_2$CH$_2$—CHRBO$_2$Diol. ψ(CH=CH) could be prepared by the methods described by Ibuka, T., Yoshizawa. H., Habashita, H., Fuji, N., Chounan, Y., Tanaka, M., and Yamamoto, Y., Tet. Lett., 1992, 33, 3783–3786 or Ibuka, T., Habashita, H., Otaka, A., Fuji, N., Oguchi. Y., Uyehara, T. and Yamamoto, Y., J.Org.Chem., 1991, 56, 4370–4382.

Other P2-P1 peptide bond replacements may be made as known in the art, such as Marraud, M., Dupont, V., Grand, V., Zerkout, S., Lecoq, A., Boussard, G., Vidal, J., Collet, A., and Aubry, A. "Modifications of the Amide Bond and Conformational Constraints in Pseudoamide Analogues", Biopolymers, 1993, 33, 1135–1148 or Gante, J. "Peptidomimetics-tailored enzyme Inhibitors", Angew.Chem.Int.Ed.Engl., 1994, 33, 1685–1698.

The reaction is preferably carried out in a dry, aprotic, polar solvent for example tetrahydrofuran, at a temperature between about −79° C. and room temperature (typically, 20° C.).

The intermediates may be obtained by the methods disclosed herein or alternatively by general methods as described in Matteson et al, Organometallics, 3, 1284–8 (1984). or as in Elgendy et al, Tet.Lett, 1992, 33, 4209–4212 or Tetrahedron 1994, 50, 3803–3812 or Rangaishenvi et al, J.Org.Chem 1991, 56, 3286–3294, or in EP-A-0599633. Suitable replaceable protecting groups may be used, for example as outlined for instance in Greene, T. W. and Wuts. P. G. M., "Protective Groups in Organic Chemistry", Wiley-Interscience, 1991. The starting amino acid(s) for the preparation of the protected peptide of intermediate may be prepared by standard, well-known methods such as those described for example in Angew. Chem. 93, 793 (1981), J.Am Chem. Soc., 109, 6881 (1987) and J Jones, "The Chemical Synthesis of Peptides". Oxford Science Publications, No. 23, Clarendon Press, Oxford 1992, or may be obtained from a variety of well known commercial sources

USE

The novel peptides according to the present invention are useful as inhibitors or substrates of various enzymes, particularly trypsin-like proteases, and may be used in vitro or in vivo for diagnostic and mechanistic studies of these enzymes. More generally, the novel peptides may be useful for research or synthetic purposes. Furthermore, because of their inhibitory action, the inhibitors are useful in the prevention or treatment of diseases caused by an excess of an enzyme in a regulatory system particularly a mammalian system, e.g. the human or animal body, for example control of the coagulation or fibrinolysis system. The pharmaceutically useful compounds have a pharmaceutically acceptable group as any N-terminal substituent (X).

The compounds of the invention which are thrombin, kallikrein, factor Xa, or factor VIIa inhibitors have anti-thrombogenic properties and may be employed when an anti-thrombogenic agent is needed. Generally, these compounds may be administered orally or parenterally to a host in an effective amount to obtain an anti-thrombogenic effect. In the case of larger mammals such as humans, the compounds may be administered alone or in combination with one or more pharmaceutical carriers or diluents at a dose of from 0.02 to 10 mg/Kg of body weight and preferably 1–100 mg/Kg, to obtain the anti-thrombogenic effect, and may be given as a single dose or in divided doses or as a sustained release formulation. When an extracorporeal blood loop is to be established for a patient, 0.1–10 mg/Kg may be administered intravenously. For use with whole blood, from 1–100 mg per litre may be provided to prevent coagulation.

Pharmaceutical diluents or carriers for human or veterinary use are well known and include sugars, starches and water, and may be used to make acceptable formulations of pharmaceutical compositions (human or veterinary) containing one or more of the subject peptides in the required pharmaceutically appropriate or effective amount or concentration. Formulations of the compounds include tablets, capsules, injectable solutions and the like.

The compounds of the invention may also be added to blood for the purpose of preventing coagulation of the blood in blood collecting or distribution containers, tubing or implantable apparatus which comes in contact with blood.

Advantages enabled by the invention include oral activity, rapid onset of activity and low toxicity. In addition, these compounds may have special utility in the treatment of individuals who are hypersensitive to compounds such as heparin or other known inhibitors of thrombin or other serine proteases.

The invention will be further described and illustrated by the Examples which now follow.

EXAMPLES

In the examples, amino acid residues are of L-configuration unless otherwise stated.

1. Cbz-D-Phe-Pro-ψ(CO$_2$)-boroethylglycine pinanediol

1-Chloropropane-pinanediol boronate ester (0.321 g, 1.25×10−3 mol) added with stirring to Cbz-D-Phe-Pro-OH (0.6 g, 1.52×10$^{-3}$ mol). When the addition had been completed, DBU (0.23 g, 1.52 mmol) in CH$_2$Cl$_2$ was added to the mixture and allowed to stir at room temperature, before being left to stir for an extended period at 4° C. before workup. The opaque liquid was washed with HCl (0.1M, 2×50 ml), NaHCO$_3$ (1%, 50 ml). The organic layer was dried by vigorous stirring over anhydrous MgSO$_4$, and filtered off, to remove the desiccant. The filtrate was concentrated under reduced pressure on a rotary evaporator, to afford a thick, viscous residue. Preliminary examination by $^1$H N.M.R. showed the required crude product. The crude sample was dissolved in a small amount of MeOH, applied to the sephadex LH20 column, and then eluted with a pump using the same solvents. The elution profile was followed with the aid of a U.V. lamp (226 nM) and recorder. The void volume, fraction 1–6. and a further bulk volume were collected. From the shape of the chromatogram, it was deemed that fractions 1–6 would be the most likely fractions in which the tripeptide may be found. The fractions were concentrated individually to afford clear slightly coloured viscous residues. One fraction containing the bulk of the material when placed under high vacuum was later afforded as a slightly crystalline product (0.269 yield of 35%). N.M.R., FABMS (Fast Atom Bombardment Mass Spectrometry) and C,H,N were very strong (good) indicators that the compound has been formed.

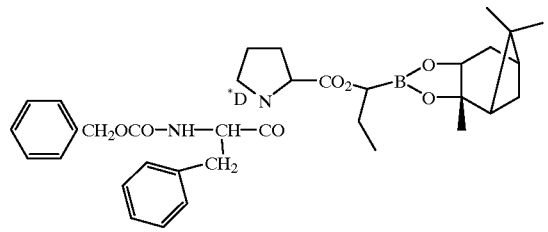

2. H-Phe-Pro-ψ(CO$_2$)-BromoEtg pinanediol

Cbz-D-Phe-Pro-ψ(CO$_2$)-BoroEtg pinanediol (from Example 1) was dissolved in MeOH (30 ml) and treated with 10% Pd/C, and purged with argon with stirring, the flask evacuated and pumped with H$_2$ with stirring for 5H. Ninhydrin staining indicated deprotected product on TLC. The solution was purged with argon for 10 min, filtered and concentrated under reduced pressure to afford a thick black oil, which was dissolved in CHCl$_3$, filtered and concentrated. $^1$H N.M.R. of the crude product indicated no protected product. The residue from above was chromatographed on a Sephadex LH20 chromatography column. $^1$H (60 MHz) N.M.R. showed that the isolated compound displayed many of the characteristics expected on the basis of the putative structure. 122 mg of the free amino boronate ester was isolated.

3. Benzyloxycarbonyl-D,L-diphenylalanylprolyl-ψ(CO₂)-borovaline pinanediol ester 1-Bromo-2-methylpropylpinanediol boronate (rmm 315, 0.630 g, 2 mmol) was dissolved in CH₂Cl₂ and subsequently treated with Cbz-D,L-Dpa-Pro-OH (rmm 472, 1.18 g, 2.5 mmol) also in CH₂Cl₂. To the mixture was added DBU (rmm 152.24, 0.381 g, 2.5 mmol) and left to stir overnight at room temperature. The organic layer was washed with HCl(0.1M, 2×50 ml) and NaHCO₃ (1%, 2×50 ml) and H₂O (2×50 ml), and dried by vigorous stirring with MgSO₄. The desiccant was filtered off and the filtrate was concentrated under reduced pressure to afford a highly crystalline residue. Examination of this material by ¹H N.M.R. (60 MHz), showed all the essential features expected on the basis of the putative structure. This "crude"(0.850, 57%) material was column chromatographed by gel filtration through Sephadex LH20, using MeOH as the eluting solvent. Gel filtration afforded a highly crystalline solid which upon observation by ¹H N.M.R. (60 MHz) was the required product (0.510 g yield of 36%). (A slower running peak was also observed, which corresponds to the unreacted boronate.)

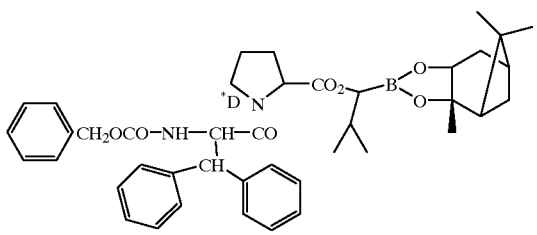

4. Cbz-D,L-Dpa-Pro-(CO₂)boroPhe-OPin

Cbz-D,L-Dpa-Pro (1 g, 2.12mmnol) was dissolved in CH₂Cl₂ (~30 ml). To the solution was added 1-bromo-2-phenylethylboronate pinanediol (rmm 363, 0.635 g, 1.75 mmol). After the addition, DBU (0.323 g, 2.12 mmol) in CH₂Cl₂ was added and the mixture left to stir overnight. The organic solution was washed with HCl (0.1M 2×50 ml), NaHCO₃ (1%, 2×50 ml) and H₂O (2×50 ml). The organic phase was dried (by stirring over MgSO₄), filtered and concentrated under reduced pressure to give the crude product (1.018 g). The crude product (1.018 g) was afforded as a thick semi-solid residue and was purified by gel filtration through Sephadex LH20. The fractions were pooled appropriately.

F1–3: 512 mg
F4: 133 mg
F5–10: 50 mg

¹H N.M.R. (60 MHz) showed that F1–3 showed most of the features expected on the basis of the putative structure.

5. Cbz-D,L-Dpa-Pro-ψ(CO₂)-1-propyl-1-boronate pinanediol 1-bromopropylboronate pinanediol ester (rmm 310, 0.542 g, 1.8 mmol) was dissolved in DCM to which was added Cbz-D,L-Dpa-Pro (1 g, 2.12 mmol). A solution of DBU (0.323 g, 2.12 mmol) in DCM was added and the mixture was stirred overnight at room temperature. The clear yellow organic solution was washed with HCl (0.1 m, 2×5 ml), NaHCO₃ (1%, 2×50 ml) and H₂O (2×5 ml). The opaque organic solution was dried by stirring over MgSO₄. The clear solution was filtered and concentrated under reduced pressure to afford a yellow solid. The crude product was chromatographed through Sephadex LH20, for further purification. The material was isolated:

F1+2: 94 mg
F3: Trace
F4: Trace
F5+6: Trace

The purified yield was actually 41% based upon the yield of the 1-bromopropylboronate pinanediol derivative.

6. Cbz-D,L-Dpa-Pro-ψ(CO₂)-BoroPgl pinanediol

Following the procedure in Example 4 above. Cbz-D,L-Dpa-Pro (0.117 g,0.2489 mmol), 1-chlorohexylboronate pinanediol (0.06 g, 0.2 mmol) and DBU (0.038 g, 0.2489 mmol) were reacted. After 144 hours the reaction was worked up as previously, to give crude solid (0.091 g, 62%). All of this material was purified further by passing through Sephadex LH20, using MeOH as eluting solvent, giving the required product (rmm 734, 95 mg ±1 mg).

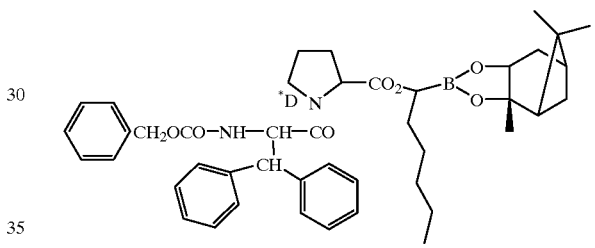

7. Cbz-D-Phe-Pro-ψ(CO₂)-boroPgl pinanediol

The same preparation method as in Example 1 above was carried out using Cbz-D-Phe-Pro (0.792 g, 2mmol), 1-chlorohexylglycine boronate (0.457 g, 1.53 mmol) and DBU (0.31 g, 2 mmol). The reaction was stirred at room temperature for 48 hours and worked up as previously to give the required product.

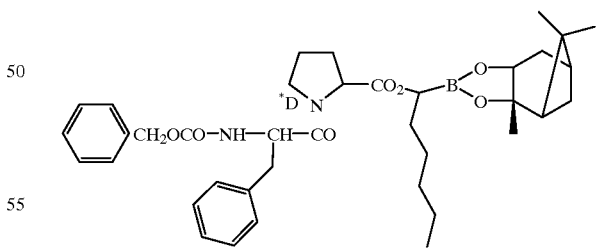

8. Cbz-D-Dpa-Pro-ψ(CO₂)-boroPhe pinanediol

The same preparative method as in Example 6 above was carried out using Cbz-D-Dpa-Pro (0.114 g. 0.242 mmol), 1-bromo-2-phenylethylboronate pinanediol (0.0726 g, 0.2 mmol) and DBU (0.368 g, 0.036 ml, 0.242 mmol). Prior to purification the required product was obtained. The actual crude yield was approximately 70 mg (yield 46%):

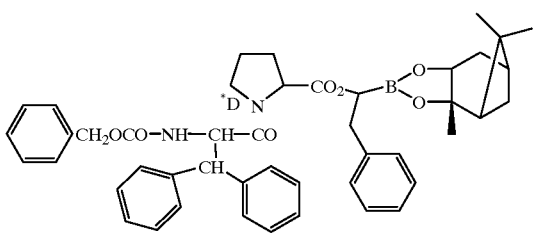

9. Preparation of Cbz-D-Phe-Pro-ψ(CO₂)-BoroPhe-OPin 1-bromo-1-benzylmethylboronate pinanediol (0.817 g, 2.25 mmol) in DCM was added, dropwise, to a solution of Cbz-D-Phe-Pro-OH (1 g, 2.53 mmol) in DCM at room temperature. After the addition DBU (0.385 g, 2.53 mmol) in DCM was added dropwise. The mixture was stirred at room temperature for 18 h, with CaCl₂ drying tube. The organic solution was washed with HCl (aq., 0.1M, 2×50 cm³), NaHCO₃ (aq, 1%, 2×50 cm³) and H₂O (2×50 cm³). The organic phase was dried by stirring over MgSO₄ (anhydrous), filtered and concentrated to give a thick viscous oil (0.72 g, 47% yield). The product was applied to a Sephadex LH20 columns, giving ten fractions:

F1–3: 237 mg
F4: 168 mg
F5–7: 165 mg
F8–10: 35 mg

Fraction 4 was submitted for elemental analysis and gave results consistent with the required product, Cbz-D-Phe-Pro-ψ(CO₂)BoroPhe-OPin (rmm 678, $C_{40}H_{47}N_2BO_7$).

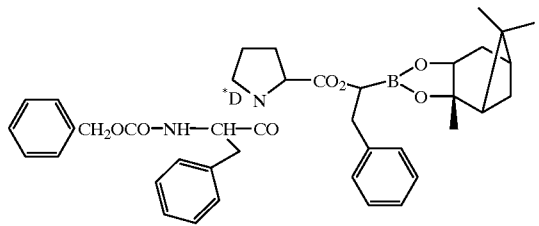

10. Preparation of Cbz-D-Phe-Pro-ψ(CH₂O)-BoroPhe-OPin

Method A

To a solution of Z-D-Phe-ProCH₂OH (273 mg, 0.86 mmol) in THF (10 ml) was added, at −78° C., lithium diisopropylamide (2 equivalents, 0.85 ml) to give a red solution. To the solution was added a precooled solution of 1-chloro-1-benzylmethyl boronate pinanediol (394 mg, 1.27 mmol, 1.5 eq.) in THF (2 ml). The solution was allowed to stir and warn to room temperature overnight, concentrated and dissolved in MeOH (1 ml) and applied to a Sephadex LH20 column (3×40 cm).

F1: trace
F2: trace
F3: trace
F4: main peak 264 mg, (46%)

F4 was found to be the required product Cbz-D-Phe-Pro-ψ(CH₂O)-BoroPhe pinanediol ester (rmm 657) and showed MS, 680 (M+Na), and a peak at 15 min on Rp HPLC (gradient 50–99% over 25 min, vydac 4.4×250 mm column).

Method B

To a solution of Cbz-D-Phe-Pro-CH₂OH (0.63 g, 1.65 mmol) in DCM was added 1-bromo-1-benzylmethylboronate pinanediol ester (0.599 g, 1.65 mmol) in DCM. Then phosphazene base P4-t-Bu ('superbase') (rmm 633.73, 1 mol. eq., 0.1046 g, 1.149 cm³, 1.65 mmol) was added as a solution in hexane, and the reaction stirred at room temperature for 18 h. The organic solution was washed with HCl (aq.,0.1M. 2×50 cm³). NaHCO₃ (aq. 1%, 2×50cm³) and H₂O (2×50 cm³). The organic phase was dried by stirring over MgSO₄ (anhydrous), filtered and concentrated to give a thick viscous oil. The product was chromatographed on Sephadex LH20 to give the required product Cbz-D-Phe-Pro-ψ(CH₂O)-BoroPhe-OPin (rmm 664).

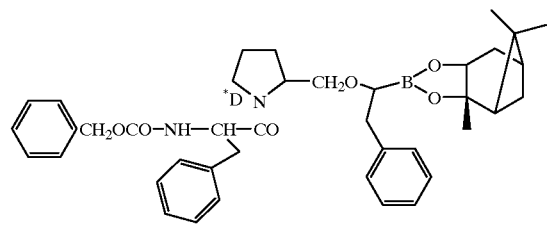

11. Preparation of 2-naphthalene sulphonylglycine-ψ(CO₂)-BoroMpg(−)OPin

2-Naphthalenesulphonyl glycine tertiary-butyl ester

To a solution of glycine tertiary-butyl ester hydrochloride (2.0 g, 12 mmol) in MeOH (10 ml) was added 2-naphthalenesulphonyl chloride (2.71 g, 12 mmol). A further 5 ml of MeOH was added to dissolve all the reagents. DBU (1.83 g, 1/79 ml, 12 mmol) was added to the mixture and allowed to stir for 18 h, under argon. The desired compound, having been authenticated by NMR, CHN and FAB-Ms (rmm 321, yield 1.23 g, 32%).

2-Naphthalenesulphonyl glycine

The tertiary butyl ester (1.351 g, 4.21 mmol) was dissolved in 95% TFA (50ml) and stirred for 1 h under argon at room temperature The solvent was then pumped off under reduced pressure, to afford a white powder. The product was authenticated by NMR, CHN, and FAB-Ms (rmm 265, yield 1.12 g, 100%).

2-Naphthalene Sulphonyl glycine-ψ(CO₂)Boro Mpg (−)OPin

1-Chloro4-methoxypropylboronate (−)pinanediol ester (0.283 g, 0.943 mmol) in THF, was added dropwise and with stirring to a solution of 2-naphthalenesulphonylglycine (0.25 g, 0.943 mmol) in THF. DBU (0.144 g. 0.943 mmol) was added to the clear solution which was allowed to stir for 18 h under argon at room temperature. A white solid had precipitated, but examination of this material by ¹H NMR showed that it was largely unreacted starting material. High field NMR examination showed a very small amount of the desired product had been formed.

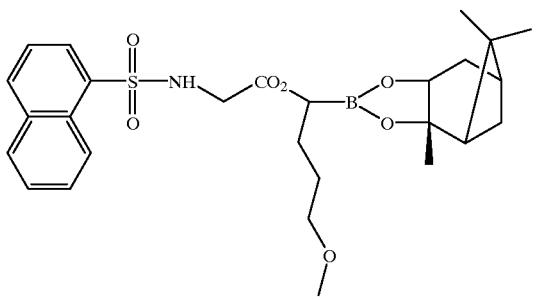

12. Preparation of Cbz-D-Dpa-Pro-ψ(CO$_2$)-GlyP(−)OPin

Chloromethylbisoxophospholane(−)pinanediol ester (−)Pinanediol (3.405 g, 0.02 mmol) was dissolved in THF (approximately 110 cm$^3$) and treated with Et$_3$N (4.048 g, 5.58 cm$^3$, 0.04 mol) before being vigorously stirred. Chloromethylphosphonic dichloride (3.347 g, 2.043 cm$^3$, 0.02 mol) in THF (approximately 100 cm$^3$) was added dropwise, with moderate stirring to the above mixture, forming a white precipitate. After the addition was complete, the mixture was left to stir at R.T. overnight. The milky suspension was filtered and the precipitate was washed with THF. The filtrate was concentrated under reduced pressure to afford a sticky white solid. $^1$H, $^{13}$C Nmr and FAB-Ms were consistent with the required product chloromethylbisoxophospholane(−)pinanediol.

Cbz-D-Dpa-Pro-ψ(CO$_2$)GlyP(−)OPin

The target compound was synthesised following the method of Example 4 using chloromethylbisoxophospholane(−)pinanediol (5.5×10$^{-4}$ mol) and Cbz-D-DpaPro (5.5×10$^{-4}$ mol). The reaction gave, after chromatography on Sephadex, the required product in 60% yield.

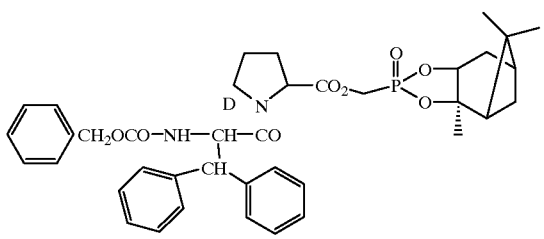

13. Preparation of Cbz-D-Dpa-Pro-ψ(COCH$_2$)BoroHpg(−)OPin

Cbz-D-Dpa-Pro-COCH$_2$Boc

Cbz-D-Dpa-Pro-OH (0.265 g, 5.6×10$^{-4}$ mol) was dissolved in THF, and cooled to 0° C. in an ice bath. CDI (N,N'-carbonyldiimidazole, 0.109 g, 6.7×10$^{-4}$ mol, 1.2 mol eq) was added with stirring to the above solution, and left for 30 min at 0° C., followed by 2 h at room temperature. The mixture was added dropwise to a precooled solution of tertiary butyl lithioacetate (formed from the addition of LDA {0.901 cm$^3$ of 2M solution, 3.2 mol eq in THF} to tertiary butyl aceate {0.21 g, 0.243 cm$^3$, 3.2 mol eq}) over 1 h at −78° C. When the addition had finished, the reaction mixture was kept at this temperature for 15 min, quenched with 1M HCl (64 cm$^3$), allowed to warm to 0° C., acidified to pH 3, and extracted with CHCl$_3$ (3×100 cm$^3$). The combined CHCl$_3$ layer was washed with saturated brine, dried over anhydrous Na$_2$SO$_4$, and concentrated under reduced pressure on a rotary evaporator. Chromatographic purification (Sephadex® LH20, MeOH) of the oily residue provided (0.215 g, 67%) of the desired compound as a yellow crystalline solid. $^1$H(CDCl$_3$) N.M.R.—good; $^{13}$C(CDCl$_3$) N.M.R.—good; ESMS(MeOH): m/z(%) 593 (M+Na, 100), 1164 (2M+H+Na).

Cbz-D-Dpa-Pro-COCH$_2$BoroHpg(−)OPin

Cbz-D-Dpa-Pro-COCH$_2$Boc (0.209 g, 3.67×10$^{-4}$ mol) was treated with NaH (1.2 mol eq) at 0° C. After 1 h α-chloro 3-methoxypropylglycine(−)pinanediol boronate ester (0.11 g, 3.67×10$^{-4}$ mol) was added and left for 2 h at 0° C. The solution was then treated with 95% TFA and stirred overnight at room temperature. The brown oily residue formed after concentration under reduced pressure on a rotary evaporator, was dissolved in EtOAc, washed with IM NaHCO$_3$, H$_2$O and brine, before being dried over anhydrous MgSO$_4$, and concentrated under reduced pressure on a rotary evaporator. Chromatographic purification (Sephadex® LH20, MeOH) of the sticky gelatinous residue afforded 0.21g (78%) of the desired compound as an orange-brown crystalline solid. $^1$H(CDCl$_3$) N.M.R.—good; $^{13}$C (CDCl$_3$) N.M.R.—good; ESMS(MeOH): m/z (%) 717(100) [M+H+].

O,O-DIALKYLDIPEPTIDYL CARBOXYPHOSPHONATES

The following Examples 15–18 describe the preparation of O,O-Dialkyldipeptidyl carboxyphosphonates. The preparation of the O,O-dialkyl-α-hydroxybenzyl phosphonates is described in Example 19.

15. Preparation of Cbz-DL-Dpa-Proψ(CO$_2$)Phg$^P$(OEt)$_2$

Cbz-DL-Dpa-Pro-OH (0.275g, 5.83×10$^{-4}$ mol) was dissolved in CH$_2$Cl$_2$, and treated with DMAP (0.0712g, 5.83×10$^{-4}$ mol). O,O-Diethyl α-hydroxybenzylphosphonate (0.129g, 5.3×10$^{-4}$ mol) was added to the mixture, followed by HOBT (0.072g, 5.3×10$^{-4}$ mol) and DCC (0.120g, 1.1 mol eq). After 30 min a white ppt (DCU) had formed. The reaction mixture was left to stir overnight. The opaque solution was then diluted with CH$_2$Cl$_2$ and filtered to remove insoluble material. The filtrate was poured onto IM NaHCO$_3$ (100cm$^3$) and extracted with EtOAc (2×100cm$^3$) and CHCl$_3$ (2×100cm$^3$). The organic extracts were combined and washed with IM HCl. The acid washings were extracted further with EtOAc, and these were added to the organic extracts. The organic layer was washed with water and brine, and then dried over anhydrous MgSO$_4$. The desiccant was filtered off, and the filtrate was concentrated under reduced pressure to afford an off-white fluffy residue. The residue was purified by chromatography through Sephadex® LH20 to afford g (%) of a fluffy white solid. $^{31}$P (CDCl$_3$): d 17.86–18.31 (dd); ESMS(MeOH): m/z (%) 699 ([M+H]+, 100).

16. Preparation of Cbz-DL-Dpa-Pro-ψ-(CO$_2$)pMeCO$_2$Phg$^P$(OEt)$_2$

The method of preparation was the same as described in Example 15. Cbz-DL-Dpa-Pro-OH (0.275g), DMAP (0.0712g, 5.83×10$^{-4}$ mol); O,O-Diethyl α-hydroxy 4-carbomethoxybenzyl-phosphonate (0.160g, 5.3×10$^{-4}$ mol); HOBT (0.072, 5.3×10$^{-4}$ mol), DCC (0.120g, 5.83× 10$^{-4}$ mol, 1.1 mol eq). The work-up was the same as in Example 15. The final compound was purified by chromatography through Sephadex® LH20. $^{31}$P(CDCl$_3$): d 17.01–17.53 (dd); ESMS(MeOH): m/z (%)

17. Preparation of Cbz-DL-Dpa-Pro-CO$_2$pNO2Phg$^P$ (OEt)$_2$

The method of preparation was the same as in Example 15. Cbz-DL-Dpa-Pro-OH (0.275g), DMAP (0.0712g), O,O-Diethyl α-hydroxy 4-nitrobenzylphosphonate (0.153g, 5.3× 10$^{-4}$ mol), HOBT (0.072g), DCC (0.120g). The work-up was the same as in Example 15. The final compound was afforded as a creamy light-yellow crystalline solid. $^{31}$P (CDCl$^3$): d 16.20–16.81 (dd); ESMS(MeOH): m/z (%) 766([M+Na]+, 100).

18. Preparation of Cbz-D-Dpa-Pro-CO$_2$ 3,4,5(MeO)$_3$Phg$^P$(OEt)$_2$

The method of preparation was the same as in Example 15. Cbz-D-Dpa-Pro-OH (0.275g), DMAP (0.0712g), O,O-Diethyl α-hydroxy 3,4,5-trimethoxybenzylphosphonate (0.177g, 5.30×10$^{-4}$ mol), HOBT (0.072g, 5.3×10$^{-4}$ mol), DCC (0.120g, 5.83×10$^{-4}$ mol). The product was afforded as a white crystalline solid. $^{31}$P(CDCl$_3$): d 17.93, 18.08 (d).

19. Preparation of O,O-dialkyl a-hydroxybenzylphosphonates

Aldehyde (0.05 mol) and dialkyl phosphite (0.05 mol) were mixed together with stirring for 10 min, under argon. Excess Al$_2$O$_3$ (approximately 30g) was added to the solution and vigorously shaken, to ensure uniform absorption onto the support. The white solid formed had become very hot, but upon cooling was allowed to stand at room temperature for 48h. The solid material was suspended in excess CH$_2$Cl$_2$ and filtered off to remove Al$_2$O$_3$. The filtrate was concentrated under reduced pressure to afford a white (or sometimes brightly colored) waxy solid.

Analytical and Activity Data

The following Tables contain analytical data and activity data relating to the invention. In the Tables, the designation "Z" denotes benzoyloxycarbonyl.

Table 1: $^{13}$C N.M.R. characterisation data for various compounds, including examples of those according to the present invention.

The carbon atom numbering used in Table 1 for the pinanediol residue is as follows:

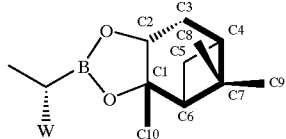

(a)

Table 2: $^1$H N.M.R. characterisation data for various compounds, including examples of those according to the present invention.

Table 3: elemental analysis

Table 4: inhibition constant (Ki) against thrombin and plasma thrombin time.

Table 5: inhibition constant (Ki) against thrombin (Thr) and elastase (Ela).

Table 6: comparative Ki data for compounds of the invention and prior art compounds.

The compounds listed in the Tables were prepared by the same or analogous methods to the compounds of the preparation Examples 1 to 12 above or, in the case of intermediates, were obtained from sources.

The following techniques were employed for activity measurement:

Plasma Thrombin Time {TT}

A volume of 150 μl of citrated normal human plasma and 20 μl of buffer or sample were warmed at 37° C. for 1 min. Coagulation was started by adding 150 μl of freshly prepared bovine thrombin (5NIHu/ml saline) and the coagulation time was recorded on a coagulometer.

A phosphate buffer, pH7.8, containing 0.1% bovine serum albumin and 0.02% sodium azide was used. The samples were dissolved in DMSO and diluted with the buffer. When no inhibitor was used DMSO was added to the buffer to the same concentration as that used in the samples. The inhibitor concentrations were plotted against the thrombin times in a semilogarithmic graph from which the inhibitor concentration that caused a doubling (40 sec) of the thrombin time was determined.

Determination of Ki

The inhibition of human α-thrombin was determined by the inhibition of the enzyme catalysed hydrolysis of three different concentrations of the chromogenic substrate S-2238.

200 μl of sample or buffer and 50 μl of S-2238 were incubated at 37° C. for 1 min and 50 μl of human α-thrombin (0.25 NIH μ/ml) was added. The initial rate of inhibited and uninhibited reactions were recorded at 4.5 nm. The increase in optical density was plotted according to the method of Lineweaver and Burke. The Km and apparent Km were determined and Ki was calculated using the relationship.

$$V = \frac{Vmax}{1 + \frac{Km}{[S]} \cdot \left(1 + \frac{[I]}{Ki}\right)}$$

The buffer used contained 0.1M sodium phosphate, 0.2M NaCl, 0.5% PEG and 0.02% sodium azide, adjusted to pH 7.5 with orthophosphoric acid.

The samples consist of the compound dissolved in DMSO.

The reader is referred to Dixon, M and Webb, E. C., "Enzymes", third edition, 1979, Academic Press, the disclosure of which is incorporated herein by reference, for a further description of the measurement of Ki.

TABLE 1

$^{13}$C N.M.R.

| | A | B | C | D | E |
|---|---|---|---|---|---|
| 1 | | pinacol Me | pinacolquat | CH3 C8,C9 | CH3 C10 |
| 2 | CH3(CH2)4BoroOPinacol | 24.82 | | | |
| 3 | MeO(CH2)3BoroOPin | | | 28.66/71, 27.03/96 | 24.02 |
| 4 | MeO(CH2)3CHClBoroOpin | | | 28.21/45/65, 27.02/09 | 23.97/24.00 |
| 5 | CH3CH(CH3)CHBrBoroOPin | | | 28.44/49, 27.05 | 24.03 |
| 6 | CH3CH2CHBrBoroOPin | | | 28/37/50, 26.98 | 23.95 |
| 7 | BrCH2CHBrBoroOpin | | | 28.30/40/58/66, 26.51 | 24.05 |
| 8 | PhCH2CHBrBoroOPin | | | 28/28/30/69, 27.02/11 | 23.97 |
| 9 | CH3(CH3)CHBrBoroOpinacol | 24.52/38 | 83.24,84.15 | | |
| 10 | Z-D-Phe-Pro-CH2OH | | | | |
| 11 | Z-D-Phe-Pro | | | | |
| 12 | Z-D-Dpa-Pro DG | | | | |
| 13 | Z-L-Dpa-Pro | | | | |
| 14 | ClCH2P(O)OPin | | | 27.87, 27.0 | 24.09 |
| 15 | ZD-Dpa-Pro(CO2)-Glyp(—)OPin DG875 | | | 27.84, 26.98 | 24.04 |
| 16 | Z-D-Phe-Pro(CO2)(CH2)3BoroOPin | | | 28.66, 27.09 | 24.01 |
| 17 | ZDPhePro(CO2)BoroEtgOPin | | | 28.52, 27.03 | 24.01 |
| 18 | ZDLDpaPra(CO2)BoroPglOPin | | | 28.47, 27.03 | 24.0/14 |
| 19 | ZDLDpaPra(CO2)BoroValOPin | | | 28.40/45, 27.00 | 23.92/99 |
| 20 | ZDPhePro(CO2)BoroPheOPin | | | 28.36/49/63, 27.00/05 | 23.98 |
| 21 | ZD-PhePro(CH2O)BoroPheOPin | | | 28.48/68, 27.01/06 | 23.96 |
| 22 | Z-Dba-Pro | | | | |
| 23 | ZDpaPro(CO2)BoroPglOPin | | | 28.47, 27.03 | 24 |
| 24 | ZDpaPro(CO2)BoroMpg(—)OPin | | | 28.46, 27.02 | 23.98 |
| 25 | ZDDpaPro(CH2O)BoroMpgOPin | | | 28.41, 27.02 | 23.99 |
| 26 | Z-L-Dpa-Pro(CO2)BoroMpgOPin | | | 28.44, 27.02 | 23.97 |
| 27 | ZNMe-PhePro(CO2)B6roMpgOPin | | | 28.42, 27.07 | 24.03 |
| 28 | | | | | |
| 30 | | | | | |

| | F | G | H | I | J | K | L | M |
|---|---|---|---|---|---|---|---|---|
| 1 | CH C4 | CH8 | CH C2 | quat C1 | quat C7 | CH2 C5 | CH2 C3 | CH2B |
| 2 | | | | | | | | 22.68, 22.46(J= ) |
| 3 | 39.20/53 | | 77.61/77.69 | 85.26/37 | 38.12 | 26.21/35/48 | 35.76 | 25.45 |
| 4 | 39.2/35/52 | | 77.60/78.53 | 85.3.6/86.72 | | 26.19/39/46 | 35.25/52 | |
| 5 | 39.37 | | 78.29 | 86.38 | 38.3 | 26.40/44/55 | 35.52/56 | |
| 6 | 39.28/48 | | 78.31 | 86.38 | 38.23 | 26.28/42 | 35.26/30 | |
| 7 | 39.33 | | 78.72 | 87.08 | 38.33/38 | 26.30/39/51 | 35.24/37 | |
| 8 | 39.34/47/51 | | 78.32 (77.7) | 85.41/86.46 | 38.05/22 | 26.08/21/38 | 35.17/44 | |
| 9 | | | | | | | | |
| 10 | | | | | | | | |
| 11 | | | | | | | | |
| 12 | | | | | | | | |
| 13 | | | | | | | | |
| 14 | 39.24 | | 81.2 | 91.58 | 38.59 | 26.02 | 34.5 | |
| 15 | 39.2 | | 81.21 | 91.61 | 38.55 | 25.99 | 34.47 | |
| 16 | 39.51 | | 77.7 | 85.6 | 38.12 | 26.49 | 35.45 | |
| 17 | 40.29 | | 78.2 | 86.34/38 | 38.16 | 26.23 | 35.28 | |
| 18 | 39.37 | | 78.51/77.24 | 86.72 | 38.2 | 26.35 | 35.29 | |
| 19 | 39.31 | | 78.25 | 86.42 | 38.26 | 26.29/37/42 | 35.32/39 | |
| 20 | 39.30/40/46 | | 77.26/66 | 84.69/85.55 | 38.09/36 | 26.31/35 | 35.41/35.65 | |
| 21 | 39.14/23 | | 78.32/48/66 | 85.51/86.65/75 | 38.06/14 | 26.33 | 35.10/39/67 | |
| 22 | | | | | | | | |
| 23 | 39.37 | | 78.51 | 86.72 | 38.2 | 26.37 | 35.3 | |
| 24 | 39.35 | | 78.54 | 86.75 | 38.22 | 26.35 | 35.27 | |
| 25 | 39.45 | | 78.5 | 86.72 | 38.25 | 26.31 | 35.24 | |
| 26 | 39.34 | | 78.75 | 86.75 | 38.22 | 26.72 | 35.28 | |
| 27 | 39.41 | | 78.25 | 86.57 | 38.16 | 26.04 | 35.2 | |
| 28 | | | | | | | | |
| 29 | | | | | | | | |
| 30 | | | | | | | | |

| | N | O | P | Q |
|---|---|---|---|---|
| 1 | CH6 | P1 side chain | Ph—CH2—OCO* | Ph quat (Phe) |
| 2 | | 23.71, 31, 62, 34.73(CH2), 14.08/13 (CH3) | | |
| 3 | | 58.42/48 (MeO), 24.14(CH2) | | |
| 4 | 51.15/28 | 58.43/50 (MeO), 24.14(CH2) | | |
| 5 | 51.27 | 21.17/26 (CH3 13) 21.44/53(CH3 14), 31.63(CH 12) | | |
| 6 | 51.2 | 27.51/61(CH3—CH—CHBr), 13.42(CH3) | | |
| 7 | 51.25 | 31.67/75 (BrCH2) | | |
| 8 | 51.24 | 139.11/19 (Ph quat), 40.51/68 (PhCH2), 125.5–129.1 (arom) | | |
| 9 | | 120.94, 115.4, | | |
| 10 | | | 66.97 | 135.86 |

TABLE 1-continued $^{13}$C N.M.R.

|    |                      |                                                              |           |                  |
|----|----------------------|--------------------------------------------------------------|-----------|------------------|
| 11 |                      |                                                              | 66.75/58  | 136.16/39/45     |
| 12 |                      |                                                              | 67.23     | 136.41           |
| 13 |                      |                                                              | 65.28/48  | 137.07/17        |
| 14 | 51.8                 |                                                              |           |                  |
| 15 | 51.77                |                                                              | 66.9      | 136.22           |
| 16 |                      | 23.224 (CH2B???), 51.25(CH)                                  | 66.81     | 136.31           |
| 17 |                      | 10.94(CH3)                                                   | 66.75     | 136.41           |
| 18 |                      | 34.19, 31.29 (CH2), 14.00(CH3)                               |           | 135.91           |
| 19 | 51.22/07, 49.39      | 21.14/41/50(CH3 A and B), 31.62(CH)                          | 66.87/91  | 136.23           |
| 20 | 51.01/20/45          |                                                              | 66.81     |                  |
| 21 |                      |                                                              | 66.92     | 135.72/93/136.25 |
| 22 |                      |                                                              | 66.58/28  | 136.22/57/80     |
| 23 | 51.17                | 14.0(CH3CH2)24.3, 26.9, 27.02(CH2)                           | 67.23     | 139.5            |
| 24 | 51.16                | 58.5(CH3, OMe) 72.1(CH2, CH2OMe) 27.3, 30.92(CH2)            | 67.1      | 139.7            |
| 25 | 51.12                | 58.42(CH3, OMe) 72.83(CH2OMe)                                | 66.7      | 139.6            |
| 26 | 51.17                | 58.50(CH3, OMe) 72.08(CH2, CH2OMe)                           | 67.17     | 139.1            |
| 27 | 51.1                 | 58.92(CH3, OMe) 67.54(CH2, CH2OMe)                           | 67.26     | 139              |
| 28 |                      |                                                              |           |                  |
| 29 |                      |                                                              |           |                  |
| 30 |                      |                                                              |           |                  |

|    | R               | S         | T        | U            | BV              | W          | X           | Y            |
|----|-----------------|-----------|----------|--------------|-----------------|------------|-------------|--------------|
| 1  | Ph quat (Z?)    | Ph quat   |          | O—CO—N/Me—CO—N | CH—CO2—CHB    | CH—CO—N    | CH—CH2—OH   | P3Ph—CH2CH   |
| 2  |                 |           |          |              |                 |            |             |              |
| 3  |                 |           |          |              |                 |            |             |              |
| 4  |                 |           |          |              |                 |            |             |              |
| 5  |                 |           |          |              |                 |            |             |              |
| 6  |                 |           |          |              |                 |            |             |              |
| 7  |                 |           |          |              |                 |            |             |              |
| 8  |                 |           |          |              |                 |            |             |              |
| 9  |                 |           |          |              |                 |            |             |              |
| 10 |                 | 163       |          | 172.19       |                 | 155.83     | 86.05       | 39.6         |
| 11 |                 |           |          | 170.76       |                 | 155.67     |             | 39.89        |
| 12 | 139.22          | 140.03    |          | 172.97       |                 | 156.3      |             |              |
| 13 | 140.61/76       | 141.30/69 |          | 172.89/96    |                 | 155.91/39  |             |              |
| 14 |                 |           |          |              |                 |            |             |              |
| 15 | 139.13/86       |           | 125–127  | 172.13/73    |                 | 155.99     |             |              |
| 16 |                 |           |          | 171.73       | 169.76          | 155.58     |             | 40.27        |
| 17 |                 |           |          | 172.48       | 169.57          | 155.53     |             | 40.3         |
| 18 | 138.54          | 139.5     |          | 174.01       | 170.79          | 155.95     |             |              |
| 19 | 139.12/38/54/88 |           |          | 172.25       |                 | 156.11     |             |              |
| 20 |                 |           |          |              |                 |            |             | 40.11/48     |
| 21 |                 | 144.35    |          | 172.01       |                 | 155.84     |             | 39.44/52     |
| 22 | 141.26          |           |          | 172.19       |                 | 156.62     |             | 36.78        |
| 23 | 138.5           | 135.91    | 126–130  | 170.79       |                 | 155.95     |             |              |
| 24 | 138.8           | 136       | 127–129  | 171.75       |                 | 155.99     |             |              |
| 25 | 136.3           | 139.86    | 126–130  | 170.14       |                 | 156.1      |             |              |
| 26 |                 |           | 124–128  |              |                 |            |             |              |
| 27 | 138             |           | 126–128  | 172.74       |                 | 156.29     |             | 36.44        |
| 28 |                 |           |          |              |                 |            |             |              |
| 29 |                 |           |          |              |                 |            |             |              |
| 30 |                 |           |          |              |                 |            |             |              |

|    | Z           | AA        | AB         | AC         | AD         | AE          | AF      | AG      | AH        | AI           |
|----|-------------|-----------|------------|------------|------------|-------------|---------|---------|-----------|--------------|
| 1  | P3-Phe-aCH  | Pro-CH    | Pro-4-CH2  | Pro-2-CH2  | Pro-3-CH2  | Dpa-aCH     | CO2H    | Dpa-bCH | Dba a-C   | Dba CH2CH2CH |
| 2  |             |           |            |            |            |             |         |         |           |              |
| 3  |             |           |            |            |            |             |         |         |           |              |
| 4  |             |           |            |            |            |             |         |         |           |              |
| 5  |             |           |            |            |            |             |         |         |           |              |
| 6  |             |           |            |            |            |             |         |         |           |              |
| 7  |             |           |            |            |            |             |         |         |           |              |
| 8  |             |           |            |            |            |             |         |         |           |              |
| 9  |             |           |            |            |            |             |         |         |           |              |
| 10 | 54.39       | 61.35     | 47.84      | 27.95      | 23.87      |             |         |         |           |              |
| 11 | 54.15       | 59.18     | 47.04      | 28.61      | 24.26      |             | 173.34  |         |           |              |
| 12 |             | 59.9      | 47.77      | 27.88      | 24.44      | 55.85       |         |         | 54.19     |              |
| 13 |             | 58.79     | 46.74      | 28.87      | 24.48      | 54.53/70/83 | 206.36  |         | 52.56     |              |
| 14 |             |           |            |            |            |             |         |         |           |              |
| 15 |             | 59.41     | 47.36      | 27.88      | 24.16      | 55.48       |         |         | 54.01     |              |
| 16 | 54.07       | 58.92     | 46.8       | 29.03      | 24.36      |             |         |         |           |              |
| 17 | 53.99/54.11 | 58.62/82  | 46.71      | 29.03/72   | 24.18/23.45 |            |         |         |           |              |
| 18 |             |           | 47.79      |            | 24.22/22.50 | 55.75      |         |         | 53.84/40  |              |
| 19 |             | 59.54/74  | 47.41      | 27.85/96   | 24.59/85   | 55.41/52    |         |         | 53.50/94  |              |
| 20 | 53.93       | 58.74     | 46.7       | 28.91      | 23.98/24.12|             |         |         |           |              |
| 21 | 54.37       | 61.19     | 47.72      | 28.48/62   | 23.82       |             |         |         |           |              |

TABLE 1-continued $^{13}$C N.M.R.

|    |       |              |              |       |       |        |       |        |              |
|----|-------|--------------|--------------|-------|-------|--------|-------|--------|--------------|
| 22 |       | 59.26        | 47.47, 49.57 | 28.43/33.51 | 24.61/77 |     | 175.75 |        | 30.68?       |
| 23 |       | 60.24        | 47.79        | 28.03 | 24.22 | 55.75  |       | 53.84  | 34.45, 25.45 |
| 24 |       | 59.89        | 47.63        | 27.31 | 24.22 | 55.65  |       | 53.91  |              |
| 25 |       | 58.5         | 47.03        | 27.3  | 24.11 | 55.14  |       | 53.78  |              |
| 26 |       | 60.26        | 47.79        | 27.34 | 24.66 | 55.16  |       | 53.84  |              |
| 27 | 58.17 | 58.92        | 46.5         | 28.75 | 24.85 |        |       |        |              |
| 28 |       |              |              |       |       |        |       |        |              |
| 29 |       |              |              |       |       |        |       |        |              |
| 30 |       |              |              |       |       |        |       |        |              |

|    | AJ |
|----|----|
|    | other |
| 1  | other |
| 2  |    |
| 3  |    |
| 4  |    |
| 5  |    |
| 6  |    |
| 7  |    |
| 8  |    |
| 9  |    |
| 10 |    |
| 11 | CH 163.06 |
| 12 | 171.51 small quat |
| 13 | 25.40, 30.55, 45.42 (CH2) 168.98/169.54 |
| 14 | 31.92, 33.41(2CH2, Cl—CH2P(O)O2) |
| 15 | 31.88, 33.38 (2CH2, CH2P(O)O2, 172.73 (quat CO2) |
| 16 |    |
| 17 |    |
| 18 |    |
| 19 |    |
| 20 | 30.07(CH2)36.35(CH2)29.48(CH3) 27.99/80(CH3) |
| 21 | 30.06(CH2), |
| 22 | 64.99, 154.21, 173.79, 41.04, 46.49, 66.28, 36.51, 31.69, 22.51, 18.27 |
| 23 | 174.01(CO2) 54.0(CH)67.23(CH2) 69.29(CH) 77.24(CH)24.1, 29.6(CH3) 29.7, 31.3, 34.2, 38.2(CH2)40.5(CH) |
| 24 | 173.3(CO2) 30.95(CH2) |
| 25 | 170.27(CO2) > 13, other strong signals |
| 26 | 30.92(CH2) 27.01(CH, CHB?), 26.34(CH2) |
| 27 | 28.38(CH3, NMe?), 23.84(CH2) 29.59/79(CH3)46.14(CH2) 168.19(quat, CO2?) |
| 28 |    |
| 29 |    |
| 30 |    |

TABLE 2

|    | A | B | C | D | E |
|----|---|---|---|---|---|
|    | Compound name | source | Dpa-aCH | Phe-aCH | Pro-aCH |
| 1  | Compound name | source | Dpa-aCH | Phe-aCH | Pro-aCH |
| 2  | Z-D-Phe-Pro-OH | 1703, 2409 dons (250,500) |  | 4.72(dd, J14.6,9.2) | 4.33(m) |
| 3  | Z-D-Dpa-Pro-OH | don 2409a(250) | 5.3(dd, J11.3, 9.4) |  | 4.08(m) |
| 4  |  | don (500) | 5.22(dd, J11.4, 8.8) |  | 4.14(m, 8.1, 9.5) |
| 5  | Z-L-Phe-Pro-OH |  |  |  |  |
| 6  | Z-L-Dpa-Pro-PH |  |  |  |  |
| 7  | L-Pms-Pro-PH | 400MHz, 13c-1Hcorreln |  |  | 4.56(m, 1H) |
| 8  | D-Pms-Pro-OH |  |  |  |  |
| 9  | Z-D-Fgl-Pro-OH |  |  |  |  |
| 10 | MeO(CH2)2CHClBO2(—)Pin | dg31/03015, 400MHz |  |  |  |
| 11 | 1Br-2Me-propylboroOPin | Se190 |  |  |  |
| 12 | ZD,LDpaPro-O-BoroPheOPin | dg311 | 5.25(dq, 1H) | 4.95? |  |
| 13 | ZD,LDpaPro-O-BoroValOPin | dg309 | 5.25(dq-M, 1H) |  |  |
| 14 | Z-DPhePro-O-BoroEtgOPin | dg339-F5 |  | 4.6 | 4.25 |
| 15 | Z-DPhePro-O-BoroPheOPin | dg305 |  |  |  |
| 16 | Z-D-Phe-ProCH2OH | jd |  | 4.65 | 4 |
| 17 |  |  |  |  |  |
| 18 |  |  |  |  |  |
| 19 |  |  |  |  |  |
| 20 |  |  |  |  |  |
| 21 |  |  |  |  |  |
| 22 |  |  |  |  |  |
| 23 |  |  |  |  |  |
| 24 |  |  |  |  |  |
| 25 |  |  |  |  |  |
| 26 |  |  |  |  |  |
| 27 |  |  |  |  |  |
| 28 |  |  |  |  |  |

TABLE 2-continued

| | F | G | H | I | J | K | L | M | N |
|---|---|---|---|---|---|---|---|---|---|
| 1 | Arg-aCH | Gly-aCH | b-Nal-aCH | Dba-aCH | aCH-B | Chg-aCH | Pms-aCH | Fgl-aCH | Dpa-bCH |
| 2 | | | | | | | | | |
| 3 | | | | | | | | | 4.40(dJ11.5) |
| 4 | | | | | | | | | 4.39(dJ11.35) |
| 5 | | | | | | | | | |
| 6 | | | | | | | | | |
| 7 | | | | | | | | 4.27(t, J, 6.6 | |
| 8 | | | | | | | | 4.22 M, 2H | |
| 9 | | | | | | | | | |
| 10 | | | | | 3.50(1H, M) | | | | |

| | O | P | Q | R | S |
|---|---|---|---|---|---|
| 1 | Phe-Bch2 | Pro-2CH2 | Pro-3CH2 | Pro-4CH2 | PhCH2O— |
| 2 | 2.96(dd, J9.7, 12.8) | 2.2, 2.58(m) | 1.53–1.8(m) | 3.54(m), 3.09(m, 1H) | 5.08(q, J19.3, 12.2) |
| 3 | | 2.2(m, 1H), 2.58(1H, m) | 1.5–1.8m, 3H | 3.78(m) | 5.0(dd, J12.4, 37.4) |
| 4 | | 2.24(m), 1.27(m) | 1.56(m), 1.78(m) | 3.7(t, ~J8.3)2.74(m, 9.5) | 5.02(dd, J12.2, 46.0) |
| 5 | | | | | |
| 6 | | | | | |
| 7 | 3.08 m, 2H | 2.05m, 2H (correln, 1spot) | 1.84, 1.74(correln, 2spots) | 3.26(m, 2H) | 4.52dd, 2H, 11.6, 90.0 |
| 8 | | 2.05 m, 2H | 1.6(m, 2H) | 3.03(m,1H), 2.86(m,1H) | 4.522H, dd, 12.0, 95.0 |
| 9 | | | | | 4.53dd, 2H, 11.7, 91.7 |
| 10 | | | | | |
| 11 | | | | | |
| 12 | | 2.25(m, 1H, 2.78(m 1H) | 1.56(m), 1.8(m) | 3.78(m), 3.0(m1H) | 5.1(d, 1H, 4.9(dd, 1H) |
| 13 | | | 1.5(m, 1H)1.7(m, 1H) | 3.78, 3.8(m, 1H) | 5.1(d,1H),4.9(dd,1H) |
| 14 | 2.9 | | | 3.5, 2.65 | 5, 1(dd) |
| 15 | 3.0(M, 2H) | | | 3.7, 3.0(m) | 5.1(d, d) |
| 16 | 3 | | 1.5, 1.25 | 3.6, 2.7 | |

| | T | U | V | W | X | Y | Z | AA |
|---|---|---|---|---|---|---|---|---|
| 1 | COCH2CH2CO | Opin-H | CH2SC(NH2)N | Ac-N | MeO | MeOCH2 | BrCH2 | PheNH |
| 2 | | | | | | | | 5.77(d, 8.54)1H |

TABLE 2-continued

| | | | | |
|---|---|---|---|---|
| 6 | | | | |
| 7 | | | | |
| 8 | | | | |
| 9 | | | | |
| 10 | 4.36(2H, ~dd) | | 3.33 | 3.41 |
| 11 | | | | |
| 12 | | | | |
| 13 | | | | |
| 14 | 4.25 | | | |
| 15 | 4.2 | | | |
| 16 | | | | |
| 17 | 4.25 | | | |
| 18 | | | | |
| 19 | | | | |
| 20 | | | | |
| 21 | | | | |
| 22 | | | | |
| 23 | | | | |
| 24 | | | | |
| 25 | | | | |
| 26 | | | | |
| 27 | | | | |
| 28 | | | | |
| 29 | | | | |
| 30 | | | | |
| 31 | | | | |

| | AB | AC | AD |
|---|---|---|---|
| 1 | Dph-NH | PrOCH2OH | 11B nmr |
| 2 | | | |
| 3 | 5.7(d, J9.1) | | |
| 4 | 5.3(d, J8.8) | | |
| 5 | | | |
| 6 | | | |
| 7 | | | |
| 8 | | | |
| 9 | | | |
| 10 | | | |
| 11 | | | (lw = 280.78Hz) |
| 12 | 5.4, 5.5(m, 0.5H) | | |
| 13 | 5.3(m, 0.5H) | | |
| 14 | | | |
| 15 | | | |
| 16 | | 3.35, 3.45 | |
| 17 | | | |
| 18 | | | |
| 19 | | | |
| 20 | | | |
| 21 | | | |
| 22 | | | |
| 23 | | | |
| 24 | | | |
| 25 | | | |
| 26 | | | |
| 27 | | | |
| 28 | | | |
| 29 | | | |
| 30 | | | |
| 31 | | | |

TABLE 3

| NAME | Calculated | C expect (found) | H expect (found) | N expect (found) | FAB:Ms:3-NOBA +NaI (M + Na) |
|---|---|---|---|---|---|
| (1)ZDPheProψ(CO$_2$)BoroEtgOPin | $C_{35}H_{45}N_2BO_7$ | 68.18(67.89) | 7.31(7.44) | 4.55(4.63) | 639(100) |
| (2)HDPheProψ(CO$_2$)BoroEtgOPin | $C_{27}H_{39}N_2BO_5$ | 67.22(67.11) | 8.09(8.29) | 5.81(5.59) | 487(100) |
| (3)ZDLDpaProψ(CO$_2$)BoroValOPin | $C_{42}H_{51}N_2BO_7$ | 71.39(68.97) | 7.22(6.75) | 3.97(4.32) | 707(M + H)(26).729(48) |
| | $C_{42}H_{51}N_2BO_7 \cdot 3/4$ HCl | 68.63(68.97) | 7.05(6.75) | 3.81(4.32) | |
| (4)F1-3ZDLDpaProψ(CO$_2$)BoroPheOPin | $C_{46}H_{51}N_2BO_7$ | 73.21(72.92) | 6.76(6.77) | 3.71(3.81) | 777(79) |
| F1-2ZDLDpaProψ(CO$_2$)propylBoroOPin | $C_{41}H_{49}N_2BO_7$ | 71.1(68.49) | 7.08(7.13) | 4.05(3.86) | 693(57), 715(15) |
| | $C_{41}H_{49}N_2BO_7 \cdot 1.5$ H$_2$O | 68.43(68.49) | 7.23(7.13) | 3.89(3.86) | |
| (5)ZDLDpaProψ(CO$_2$)BoroPglOPin | $C_{44}H_{55}N_2BO_7$ | 71.94(70.82) | 7.49(7.66) | 3.82(3.88) | 757(7) |
| (7)ZDDpaProψ(CO$_2$)BoroPheOPin | $C_{46}H_{51}N_2BO_7$ | 73.21(70.13) | 6.76(7.17) | 3.71(3.66) | 755(32).777(29) |
| | $C_{46}H_{51}N_2BO_7 \cdot 2$ H$_2$O | 69.87(70.13) | 6.96(7.17) | 3.54(3.66) | |

TABLE 3-continued

| NAME | Calculated | C expect (found) | H expect (found) | N expect (found) | FAB:Ms:3-NOBA +NaI (M + Na) |
|---|---|---|---|---|---|
| (8)ZDPheProψ(CO$_2$)BoroPheOPin | C$_{40}$H$_{47}$N$_2$BO$_7$ | 70.8(70.82) | 6.93(6.96) | 4.13(3.70) | 701(100) |
| (9)ZDPheProψ(CH$_2$O)BoroPheOPin | | | | | 687(100), 405(94) |
| (10)2NapthylSO$_2$GlyOtBu | C$_{16}$H$_{19}$NSO$_4$ | 59.81(59.71) | 5.92(5.95) | 4.36(4.40) | 266(M + H)(55) |
| 2NapthylSO$_2$Gly | C$_{12}$H$_{11}$NSO$_4$ | 54.34(54.39) | 4.15(4.16) | 5.28(5.32) | 322(M + H, 94).266(100) |
| (11)ZDDpaProψ(CH$_2$O)BoroMpgOPin | | | | | 745.3(ES-Ms) |

NOBA = meta-nitrobenzyl alcohol
M + Na = molecular weight + Na molecular weight
ES = electrospray mass spectroscopy

TABLE 4

| | Ki(thrombin) (microM) |
|---|---|
| 85 Z-D-Phe-Pro-(CO$_2$)BoroEtg-OPin | 0.269 |
| 87 Z-D,L-Dpa-Pro-(CO$_2$)BoroVal-OPin | 18.2 |
| 88 Z-D-Phe-Pro-(CO$_2$)BoroPhe-OPin | 0.129 |
| 89 Z-D,L-Dpa-Pro-(CO$_2$)BoroPheOPin | 0.039 |
| 90 Z-D,L-Dpa-Pro-(CO$_2$)BoroEtg-OPin | 0.247 |
| 91 Z-D-Dpa-Pro-(CO$_2$)BoroPhe-OPin | 0.0392 |
| 100 Z-D-Phe-Pro(CO$_2$)BoroPglOPin | 0.088 |
| 101 Z-D,L-DpaPro(CO$_2$)BoroPglOPin | 0.131 |
| 102 Z-D-Phe-Pro(CH$_2$O)BoroPheOPin | 0.148 |
| 109 Z-D,L-Dpa-(CO$_2$)BoroMpgOPin | 0.435 |
| 116 Z-D-Dpa-Pro(CO$_2$)-L-BoroMpgOPin | 0.283 |
| 173 Z-D-Dpa-Pro-(CH$_2$O)-L-BoroMpg-OPin | 2.39 |
| 177 Z-D-Dpa-Pro-(CO$_2$)-Glyp(–)OPin | 13.7 |
| 239 Z-D,L-Dpa-Pro-(CO$_2$)(pNO$_2$)Phgp(OEt)$_2$ | 6.2 |
| 264 Z-D,L-Dpa-Pro-(CO$_2$)-Phgp(OEt)$_2$ | 16 |
| 270 Z-D-Dpa-Pro(COCH$_2$)-BoroHpg(–)OPin | 0.292 |

TABLE 5

| | Thr Ki(microM) | Ela(microM) |
|---|---|---|
| Z-D,L-Dpa-Pro-(CO$_2$)BoroEtg-OPin | 0.247 | 4.5 |
| Z-D,L-Dpa-Pro-(CO$_2$)BoroVal-OPin | 18.2 | 55 |
| Z-D-Phe-Pro-(CO$_2$)BoroEtg-OPin | 0.269 | 0.087 |

TABLE 6

| | Ki(thrombin) | Ki(elastase) |
|---|---|---|
| Z-D-Phe-Pro(CO$_2$)BoroEtgOPin | 0.269 | 0.087 |
| Z-D-Phe-ProBoroEtgOPin | 1.000 | 0.561 |
| Z-D,L-Dpa-Pro-BoroPhe-OPin | 0.082 | — |
| Z-D,L-Dpa-Pro-(CO$_2$)BoroPhe-OPin | 0.039 | — |
| Z-D,L-Dpa-Pro(CO$_2$)BoroVal-OPin | — | 55 |
| Z-D-Dpa-Pro-BoroVal-OPin | — | >70.8 |

We claim:

1. A peptidyl serine protease inhibitor characterised in that the P2-P1 natural peptide linkage is replaced by a linkage other than an N-substituted natural peptide linkage.

2. An inhibitor of claim 1, wherein the group at the carboxy position of the P1 residue is a boron acid group or phosphorus acid group or a derivative thereof.

3. An inhibitor of claim 1, wherein the group at the carboxy position of the P1 residue is of the formula III:

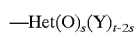

wherein

Het is a heteroatom;

s is 0, 1 or 2;

t is the valency of Het, t-2s being an integer of at least 1, and each Y is independently hydrogen, halogen, hydroxy, substituted hydroxy, substituted thiol, amino or substituted amino, wherein two hydroxy groups, two thiol groups or an amino group are/is optionally substituted by a single divalent substituent.

4. An inhibitor of claim 3, wherein Het is boron or phosphorus.

5. An inhibitor of claim 4, wherein each Y is independently F or other halogen, OΣ$^1$ or NΣ$^1$Σ$^2$, wherein Σ$^1$ and Σ$^2$ are independently selected from H, hydrocarbyl and hydrocarbylcarbonyl, the hydrocarbyl groups optionally being substituted by one or more moieties selected from halogen, OH or alkoxy and/or containing an ether or ester linkage (—O— or —COO—), which groups contain up to 20 carbon atoms or wherein two Y groups taken together form the residue of a diol or a dithiol.

6. An inhibitor of claim 1, wherein the replacement linkage has a chain length of from 1 to 5 atoms.

7. An inhibitor of claim 6, wherein said replacement linkage is —CO$_2$—, —CH$_2$O—, —NHCO—, —CHYCH$_2$—, —CH═CH—, —CO(CH$_2$)$_p$CO— where p is 1, 2 or 3, —COCHY—, —CO$_2$—CH$_2$NH—, —CHY—NX—, —N(X)CH$_2$—N(X)CO—, —CH═C(CN)CO—, —CH(OH)—NH—, —CH(CN)—NH—, —CH(OH)—CH$_2$ or —NY—CHOH—, where X is H or an amino protecting group and Y is H or halogen.

8. An inhibitor of claim 7, wherein said replacement linkage is —CO$_2$— or —CH$_2$O—.

9. An inhibitor of claim 1 which is a trypsin-like protease inhibitor.

10. An inhibitor of claim 9, wherein:

there are from 3 to 6 amino acid residues, which amino acids may be natural or unnatural, the P1 residue is a residue of Arg, Lys, Gpa, amidinoPgl or amidinopiperidylglycine or is a residue of an amino acid with a side chain which is C1–C6 alkyl, C1–C6 haloalkyl, alkoxyalkyl containing from 2 to 6 carbon atoms, or a moiety containing a 5 to 10 member (hetero)aryl group and optionally a total number of alkyl and/or alkylene carbon atoms not exceeding 4, the P2 residue is a residue of Pro, 2- or 3-thioproline or pipecolic acid and the P3 residue is a residue of D-Phe; D-Phe substituted at the phenyl 2-position by C$_1$–C$_6$ alkyl, C$_1$–C$_6$ alkyl, C$_1$–C$_6$ acyl or by aryl; D-Dpa; Dba; Pms; α- or β- NaI: TMSal; Chg; Phg; D-Tiq; or a para ether of D-Tyr.

11. An inhibitor of claim 9, wherein:

there are 2 amino acid residues, which amino acids may be natural or unnatural, the P1 residue is a residue of Arg, Lys, Gpa, amidinoPgl or amidinopiperidylglycine or is a residue of an amino acid with a side chain which is $C_1-C_6$ alkyl, $C_1-C_6$ haloalkyl, alkoxyalkyl containing from 2 to 6 carbon atoms, or a moiety containing a 5 to 10 member (hetero)aryl group and optionally a total number of alkyl and/or alkylene carbon atoms not exceeding 4 and the P2 residue has a N-terminal protecting group which is naphthylsulfonyl.

12. A compound of the formula:

wherein the aforegoing symbols are as defined below, in which definitions "aryl" encompasses heteroaryl and "alkyl" encompasses cycloalkyl:

X is H or an amino protecting group and is bonded to the amino group of the N-terminal amino acid;

m is an integer of from 0 to 5;

n is 0 or 1, provided that if n and m are both 0 then X is a group of the formula $R^{10}(CH_2)_eCOO-$ or $R^{10}(CH_2)_eSO_2-$ wherein e is 0 to 3 and $R^{10}$ is a $C_5-C_{12}$ aryl, arylalkyl or alkylaryl group optionally substituted by halogen or —OH;

ψ is —CO$_2$—, —CH$_2$O—, —NHCO—, —CHYCH$_2$—, —CH=CH—, —CO(CH$_2$)$_p$CO— where p is 1, 2 or 3, —COCHY—, —CO$_2$—CH$_2$NH—, —CHY—NX—, —N(X)CH$_2$—N(X)CO—, —CH=C(CN)CO—, —CH(OH)—NH—, —CH(CN)—NH—, —CH(OH)—CH$_2$— or —NH—CHOH—, where X is H or an amino protecting group and Y is H or F;

aa$^1$, aa$^2$, aa$^3$ and aa$^4$ are each independently a residue of a natural or an unnatural amino acid or a group of the formula

wherein

W$^1$ and W$^2$ are each independently selected from

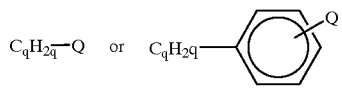

(i)

where Q=amino, amidino, imidazole, guanidino, N$_3$, or isothioureido, and q is an integer of from 1 to 5;

(ii) a side chain of a natural amino acid; or (iii) a group of the formula V or VI:

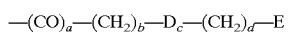 V

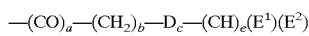 VI wherein a is 0 or 1;

e is 1;

b and d are independently 0 or an integer such that (b+d) is from 0 to 4; and (b+e) is from 1 to 4;

c is 0 or 1;

D is O or S;

E is H, $C_1-C_6$ alkyl, or a saturated or unsaturated cyclic group which is a 5–6 membered ring, or an 8–14 membered fused ring system, which alkyl or cyclic group is optionally substituted by up to 3 groups independently selected from —R$^{13}$, —R$^1$OR$^{13}$, —R$^1$COR$^{13}$, —R$^1$CO$_2$R$^{13}$ and R$^1$O$_2$CR$^{13}$, wherein R$^1$ is —(CH$_2$)$_f$ and R$^{13}$ is —(CH$_2$)$_g$H or a moiety which has a total number of carbon and heteroatoms from 5 to 10 and which contains a ring system and optionally an alkyl and/or an alkylene group, where f and g are each independently from 0 to 10, provided that (f+g) does not exceed 10, and provided that there is only a single substituent if the substituent group is a said moiety containing a ring system, or E is $C_1-C_6$ trialkylsilyl; and E$^1$ and E$^2$ are each independently a 5 or 6 membered ring;

in which group of Formula V or VI any one or more hydrogen atoms bonded to a carbon atom is optionally replaced by halogen;

or wherein W$^1$ and W$^2$ together with the carbon atom to which they are bonded form a ring system, W$^1$ and W$^2$ together form an alkenyl or aralkenyl group, or —HNC(W$^1$)(W$^2$)CO— is the residue of an amino acid in which W$^1$ is H and W$^2$ is a group which together with the α-amino group forms a cyclic group which is a 4–6 membered ring or an 8–10 membered fused ring system optionally substituted by up to 3 groups independently selected from —R$^{13}$, —R$^1$OR$^{13}$, R$^1$COR$^{13}$, —R$^1$CO$_2$R$^{13}$ and —R$^1$O$_2$CR$^{13}$, wherein R$^1$ and R$^{13}$ are as hereinbefore defined and any one or more hydrogen atoms bonded to a carbon atom is optionally replaced by halogen; and

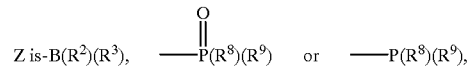

where: R$^2$ and R$^3$ are each independently selected from halogen, —OH, —OR$^4$ and —NR$^4$R$^5$, where R$^4$ and R$^5$ are each independently a group of the formula R$^6$(CO)$_u$—, wherein u is 0 or 1 and R$^6$ is H or an optionally halogenated alkyl, aryl or arylalkyl group containing up to (10-u) carbon atoms and optionally substituted by one or more groups selected from OH, R$^7$(CO)$_v$O— and R$^7$(CO)$_v$—, wherein v is 0 or 1 and R$^7$ is C1–C$_{6-V}$ alkyl, or is an aryl, alkylaryl, arylalkyl or alkylarylalkyl group containing up to (10-v) carbon atoms;

or R$^2$ and R$^3$ taken together represent a residue of a diol or a dithiol;

R$^8$ is selected from the group consisting of R$^2$, R$^3$, R$^4$ and R$^5$; and R$^9$ is a group selected from the following: —H, —OR$^4$, OR$^5$, provided that when aa$^1$ is glycine, then aa$^2$ is not a group of the formula —HNC(W$^1$)W$^2$)CO— wherein one of W$^1$ and W$^2$ is a group as defined in clause (i) above.

13. A compound of claim 12 wherein ψ is —CO$_2$— or —CH$_2$O—.

14. A compound of claim 12, wherein R$_2$ and R$_3$ together represent the residue of a diol or a dithiol and said diol or dithiol comprises two or more OH or SH groups, respectively, separated by at least two connecting atoms in a $C_2-C_{10}$ straight or branched chain or ring hydrocarbyl group optionally interrupted by one or two hetero atoms selected from N, S, and O and/or substituted by one or more inert substituents.

15. A compound of claim 12, wherein Z is —B(R$^2$)(R$^3$) in which R$^2$ and R$^3$ are both —OH or together form a residue of a diol which is pinanediol, pinacol, perfluoropinacol, ethylene glycol, diethylene glycol, catechol, 1,2-cyclohexanediol, 1,2-cyclohexaneethanediol, 1,3- propanediol, 2,3-butanediol, 1,2-butanediol, 1,4-butanediol, 2,3-dimethylbutane-2,3-diol, glycerol, or diethanolamine or another amino dihydroxy alcohol.

16. A compound of claim 15, wherein $R^2$ and $R^3$ together form a pinacol or a pinanediol residue.

17. A compound of claim 12, wherein (i) m is 0 and n is 1 or n is 0 and (ii) $R^{10}$ is phenyl, naphthyl, $C_1$–$C_4$ alkylphenyl or phenyl $C_1$–$C_4$ alkyl.

18. A compound of claim 12, wherein n is 1 and $aa^3$ is the residue of a natural hydrophobic amino acid or is a residue of a group of the formula

C(NHV)COOH wherein $Ar^1$ and $Ar^2$ are each independently selected from the group consisting of H; phenyl; phenyl substituted by halogen, a $C_1$–$C_6$ group which is alkyl or alkyl substituted or interrupted by a carbonyl or carbonyloxy group (e.g., alkylcarbonyl or alkoxycarbonyl) or substituted by —$R^{14}$ or —$OR^{14}$ wherein $R^{14}$ is a 5- or 6-membered aromatic or non-aromatic ring or is $C_1$–$C_4$ alkyl substituted by such a 6-membered ring; bipyridyl; furanyl; chromanyl; quinolinyl; thienyl; pyridyl; α- or β-naphthyl; thionaphthyl; indolyl; p-iodophenylalanyl; diphenyl-methyl; fluorenyl; wholly or partially saturated groups corresponding to any of these; $Me_3Si$; or 2,2,2-trichloroethyl; any of the foregoing groups optionally being substituted by up to three groups selected from $C_1$–$C_3$ alkyl, $C_1$–$C_3$ alkoxy, $R^{13a}CO$— wherein $R^{13a}$ is H, $CH_3$ or $C_2H_5$, $R^{13a}OR^{1a}$— or $R^{13a}COR^{1a}$—, wherein $R^{1a}$ is —$CH_2$—, —$C_2H_4$— or —$C_3H_6$—, $L^1$ and $L^2$ are each independently selected from the group consisting of $CH_2$, $CH_2$—$CH_2$, O—$CH_2$, S—$CH_2$, and a bond, and V is H, or —NHV and one of $Ar^1$—$L^1$ and $Ar^2$—$L^2$ together form a group of the formula

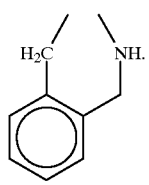

19. A compound of claim 12, wherein n is 1 and $aa^3$ is a residue of D-Phe; D-Phe substituted at the phenyl 2-position (i) by a $C_1$–$C_6$ group which is alkyl or alkyl substituted or interrupted by a carbonyl or carbonyloxy group (e.g. is alkylcarbonyl or alkyloxycarbonyl) or (ii) by a 5 or 6 membered aryl group; D-Dpa; Dba; Pms; α- or β- Nal; TMSal; Chg; Phg; D-Tiq; or a para ether of D-Tyr or wherein n and m are both 0 and X is naphthylsulfonyl glycine.

20. A compound of claim 12, wherein $aa^2$ is a residue of a group of the formula VIII

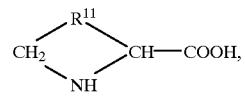

VIII where $R^{11}$ is —$CH_2$—, —$CH_2$—$CH_2$—, —S—$CH_2$—, —S—$C(CH_3)_2$— or —$CH_2$—$CH_2$—$CH_2$—, which group is optionally substituted at one or more —$CH_2$— groups by from 1 to 3 $C_1$–$C_3$ alkyl groups.

21. A compound of claim 20, wherein $aa^2$ is the residue of proline, 2- or 3-thioproline or pipecolic acid.

22. A compound of claim 12, wherein $aa^1$ is a group of the formula —$HNC(W^1)(W^2)CO$— wherein $W^2$ is H and $W^1$ is

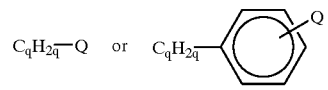

wherein q is 3, 4 or 5 and Q is amino, amidino, imidazole, guanidino, $N_3$ or isothioureido; or $W^1$ is a group of formula V of claim 12 wherein a is 0, and the total number of carbon atoms and heteroatoms does not exceed 10 or is a group of formula V of claim 12 wherein a is 0, D is O and E is H, $C_1$–$C_6$ alkyl, $C_1$–$C_6$ haloalkyl, $C_1$–$C_6$ trialkylsilyl or $C_6$–$C_{10}$ aryl optionally substituted by up to three groups selected from $C_1$–$C_4$ alkyl, halogen and $C_1$–$C_4$ alkoxy.

23. A compound of claim 22, wherein $aa^1$ is the residue of Arg, Lys, Gpa, amidinoPgl or amidinopiperidylglycine or of an amino acid with a side chain which is $C_1$–$C_6$ alkyl, $C_1$–$C_6$ haloalkyl, alkoxyalkyl containing from 2 to 6 carbon atoms, or a moiety containing a 5 to 10 member aryl group and optionally up to 4 alkyl or alkylene carbon atoms.

24. A compound of claims 12, which has an $(aa^4)$-$aa^3$-$aa^2$ sequence as shown in the following Table:

| Residue Sequence |
| --- |
| ProPhe |
| AlaPro, LeuPro, AlaAla, LysLeu, GlyAla |
| IleuGluGly, PyroGluGly, ArgGly, ChaGly |
| L-PhePhe, NalPhe, D-TiqPhe, NalThr, NalPhg |
| GlyPhe, IlePro |
| PhePro, GluGly |

25. A compound of claim 12, wherein an additional natural peptide linkage to the $aa^2$-$aa^1$ linkage is replaced by a said ψ group.

26. A compound of the formula II:

W-ψ-A-Z    II, wherein
A is a group selected to have affinity for the specificity pocket of a serine protease, W is a moiety selected to have affinity for a binding site of a serine protease, ψ is a linker other than a natural peptide group or an N-substituted natural peptide group, and Z is a moiety which interacts with the active site triad residues of a serine protease.

27. An inhibitor of claim 9 or a compound of claim 12 or 26 which has affinity for thrombin and includes a thrombin anion exosite association moiety.

28. An inhibitor of claim 4 or a compound of claim 12 or 26 which is in the form of a pharmaceutically acceptable salt thereof and/or which comprises one or more protectable functional groups protected by a pharmaceutically acceptable protecting group.

29. A compound of claim 12 or 26, which has affinity for a trypsin-like protease.

30. A compound of claim 26 which has affinity for a chymorypsin-like protease.

31. An inhibitor of claim 4 or a compound of claim 12 or 26 which has affinity for kallikrein, elastase, Factor Xa, Factor VIIa, plasmin or urokinase.

32. An inhibitor of claim 4 or a compound of claim 12 or 26 which has a Ki at 37° C. for a serine protease of 0.5 μM or less.

33. An inhibitor or compound of claim 32, wherein said Ki is 0.1 μM or less.

34. An inhibitor of claim 4 or a compound of claims 12 or 26 which has a Ki at 37° C. for a single serine protease which is 0.5 μM or less than the Ki values for all other serine proteases.

35. A pharmaceutical formulation comprising an inhibitor of claim 4 or a compound of claim 12 or 26 formulated for use as a human or veterinary pharmaceutical.

36. A pharmaceutical composition comprising an inhibitor of claim 4 or a compound of claim 12 or 26 and a pharmaceutically acceptable diluent, excipient or carrier.

37. A method of treating by therapy or prophylaxis a bodily disease or disorder capable of treatment by inhibition of a serine protease, comprising administering, e.g. orally or parenterally, to a human or animal patient a therapeutically or prophylactically effective amount of an inhibitor of claim 4 or a compound of claim 12 or 26.

38. A method of treating by therapy or prophylaxis a bodily disease or disorder capable of treatment by inhibition of a serine protease, comprising administering to a human or animal patient a therapeutically or prophylactically effective amount of an inhibitor of claim 4, which inhibitor has a P1 residue with affinity for a specificity pocket of the serine protease and a subsite binding domain selective for a binding site of said serine protease.

39. A method of preparing a compound of claim 26 which comprises reacting together a compound of the formula W—G$^1$ and a compound of the formula G$^2$—A—2, wherein G$^1$ and G$^2$ are groups which may be reacted together to form a linking group other than a natural amide bond.

40. A compound of the formula X—(aa$^4$)$_m$—(aa$^3$)$_n$—(aa$^2$)—G$^1$ or G$^2$—(aa$^1$)—Z, wherein (aa$^1$), (aa$^2$), (aa$^3$), (aa$^4$), X, Z, m and n are as defined in claim 12 and G$^2$ are each a group capable of reacting with a group on another molecule to form a linking group other than a natural amide bond.

41. A compound of claim 40, which is of the formula

Lg—(aa$^1$)—Z,

M$^+$—(aa$^1$)—Z,

X—(aa$^4$)$_m$—(aa$^3$)$_n$—(aa$^2$)—CH$_2$OH, or

X—(aa$^4$)$_m$—(aa$^3$)$_n$—(aa$^2$)—COCH$_2$Lg wherein Lg is a leaving group and M$^+$ is an alkali metal ion or another cation.

42. An inhibitor of claim 4, wherein said replacement linkage is —CO$_2$—, —CH$_2$O—, —NHCO—, —CHYCH$_2$—, —CH═CH—, —CO(CH$_2$)$_p$CO— where p is 1, 2 or 3 —COCHY—, —CO$_2$—CH$_2$NH—, —CHY—NX—, —N(X)CH$_2$—N(X)CO—, —CH═C(CN)CO—, —CH(OH)—NH—, CH(CN)—NH—, —CH(OH)—CH$_2$ or —NH—CHOH—, where X is H or an amino protecting group and Y is H or F.

43. An inhibitor of claim 42, wherein said replacement linkage is —CO$_2$— or —CH$_2$O—.

44. An inhibitor of claim 43, wherein:

there are from 3 to 6 amino acid residues, which amino acids may be natural or unnatural, the P1 residue is of Arg, Lys, Gpa, amidinoPg1 or amidinopiperidylglycine or is a residue of an amino acid with a side chain which is C$_1$–C$_6$ alkyl, C$_1$–C$_6$ haloalkyl, alkoxyalkyl containing from 2 to 6 carbon atoms, or a moiety containing a 5 to 10 member (hetero)aryl group and optionally a total number of alkyl and/or alkylene carbon atoms not exceeding 4, the P2 residue is of Pro, 2- or 3- thioproline or pipecolic acid and the P3 residue is of D-Phe; D-Phe substituted at the phenyl 2-position by 1C–6C alkyl, 1C–6C acyl or by aryl; D-Dpa; Dba; Pms; α- or β- Nal; TMSal; Chg; Phg; D-Tiq; or a para ether of D-Tyr.

45. A compound of claim 12 wherein:

n is 1;

aa$^3$ is the residue of a natural hydrophobic amino acid or is a residue of a group of the formula:

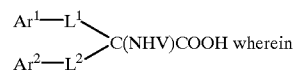C(NHV)COOH wherein wherein

Ar$^1$ and Ar$^2$ are each independently selected from the group consisting of H; phenyl; phenyl substituted by halogen, a C$_1$–C$_6$ group which is alkyl or alkyl substituted or interrupted by a carbonyl or carbonyloxy group or substituted by —R$^{14}$ or —OR$^{14}$ wherein R$^{14}$ is a 5 or 6 membered aromatic or non-aromatic ring or is C$_1$–C$_4$ alkyl substituted by such a 6 membered ring; bipyridyl; furanyl; chromanyl; quinolinyl; thienyl; pyridyl; α or β-naphthyl; thionaphthyl; indolyl; p-iodophenylalanyl; diphenyl-methyl; fluorenyl; wholly or partially saturated groups corresponding to any of these; Me$_3$Si; or 2,2,2-trichloroethyl; any of the foregoing groups optionally being substituted by up to three groups selected from C$_1$–C$_3$ alkyl, C$_1$–C$_3$ alkoxy, R$^{13a}$CO— wherein R$^{13a}$ is H, CH$_3$ or C$_2$H$_5$, R$^{13a}$OR$^{1a}$— or R$^{13a}$COR$^{1a}$—, wherein R$^{1a}$ is —CH$_2$—, —C$_2$H$_4$— or —C$_3$H$_6$—, L$^1$ and L$^2$ are each independently selected from the group consisting of CH$_2$, CH$_2$—CH$_2$, O—CH$_2$, S—CH$_2$, and a bond, and V is H, or —NHV and one of Ar$^1$-L$^1$ and Ar$^2$-L$^2$ together form a group of the formula

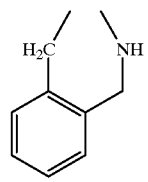

and aa² is a residue of a group of the formula VIII

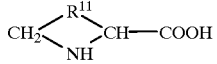

VIII where R¹¹ is —CH₂—, CH₂—CH₂—, —S—CH₂—, —S—C(CH₃)₂— or —CH₂CH₂—CH₂—, which group is optionally substituted at one or more —CH₂— groups by from 1 to 3 C₁-C₃ alkyl groups.

46. A compound of claim 43 which is in the form of a pharmaceutically acceptable salt thereof and/or which comprises one or more protectable functional groups protected by a pharmaceutically acceptable protecting group.

47. A method of treating by therapy or prophylaxis a bodily disease or disorder capable of treatment by inhibition of a serine protease, comprising administering to a human patient a therapeutically or prophylactically effective amount of an inhibitor of claim 43.

48. A method of inhibiting a serine protease comprising contacting the serine protease with a serine protease inhibitor of claim 4, wherein the inhibitor has a P1 residue with affinity for a specificity pocket of the enzyme and a subsite binding domain with affinity for a binding site of the enzyme.

49. A method of inhibiting coagulation in an extracorporeal blood loop established for a patient comprising administering to the patient an amount of an inhibitor of claim 4 effective to inhibit coagulation.

50. A method of inhibiting coagulation of blood in a container comprising contacting the blood with an amount of an inhibitor of claim 4 effective to inhibit coagulation.

51. A compound of claim 12, wherein:

n is 1;

aa³ is the residue of a natural hydrophobic amino acid or is a residue of a group of the formula

Ar¹ and Ar² are each independently selected from the group consisting of H; phenyl; phenyl substituted by halogen, a C₁-C₆ group which is alkyl or alkyl substituted or interrupted by a carbonyl or carbonyloxy group (e.g., alkylcarbonyl or alkoxycarbonyl) or substituted by —R¹⁴ or —OR¹⁴ wherein R¹⁴ is a 5- or 6-membered aromatic or non-aromatic ring or is C₁-C₄ alkyl substituted by such a 6-membered ring; bipyridyl; furanyl; chromanyl; quinolinyl; thienyl; pyridyl; α- or β-naphthyl; thionaphthyl; indolyl; p-iodophenylalanyl; diphenyl-methyl; fluorenyl; wholly or partially saturated groups corresponding to any of these; Me₃Si; or 2,2,2-trichloroethyl; any of the foregoing groups optionally being substituted by up to three groups selected from C₁-C₃ alkyl, C₁-C₃ alkoxy, R¹³ᵃCO— wherein R¹³ᵃ is H, CH₃ or C₂H₅, R¹³ᵃOR¹ᵃ— or R¹³ᵃCOR¹ᵃ—, wherein R¹ᵃ is —CH₂—, —C₂H₄— or —C₃H₆—, L¹ and L² are each independently selected from the group consisting of CH₂, CH₂—CH₂, O—CH₂, S—CH₂, and a bond, and V is H, or —NHV and one of Ar¹-L¹ and Ar²-L² together form a group of the formula

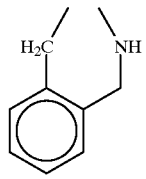

or aa³ is a residue of D-Phe; D-Phe substituted at the phenyl 2-position (i) by a C₁-C₆ group which is alkyl or alkyl substituted or interrupted by a carbonyl or carbonyloxy group (e.g. is alkylcarbonyl or alkyloxycarbonyl) or (ii) by a 5 or 6 membered aryl group; D-Dpa; Dba; Pms; α- or β- Nal; TMSal; Chg; Phg; D-Tiq; or a para ether of D-Tyr or wherein n and m are both 0 and X is naphthylsulfonyl glycine;

aa² is a residue of a group of the formula VIII

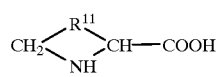

VIII where R¹¹ is —CH₂—, —CH₂—CH₂—, —S—CH₂, —S—C(CH₃)₂— or —CH₂—CH₂—CH₂—, which group is optionally substituted at one or more —CH₂— groups by from 1 to 3 C₁-C₃ alkyl groups, or is the residue of proline, 2- or 3-thioproline or of pipecolic acid; and aa¹ is a group of the formula —HNC(W¹)(W²)CO— wherein W² is H and W¹ is

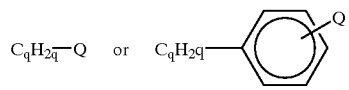

wherein q is 3, 4 or 5 and Q is amino, amidino, imidazole, guanidino, N₃ or isothioureido; or W¹ is a group of formula V of claim 12 wherein a is 0, D is O and E is H, C₁-C₆ alkyl, C₁-C₆ haloalkyl, C₁-C₆ trialkylsilyl or C₆-C₁₀ aryl optionally substituted by up to three groups selected from C₁-C₄ alkyl, halogen and C₁-C₄ alkoxy and optionally wherein m is 0.

52. A compound of claim 26 wherein:

Z is —B(R²)(R³);

where: R² and R³ are each independently selected from halogen, —OH, —OR⁴ and —NR⁴R⁵, where R⁴ and R⁵ are each independently a group of the formula R⁶(CO)ᵤ—, wherein u is 0 or 1 and R⁶ is H or an optionally halogenated alkyl, aryl or arylalkyl group containing up to (10-u) carbon atoms and optionally substituted by one or more groups selected from OH, R⁷(CO)ᵥO— and R⁷(CO)ᵥ—, wherein v is 0 or 1 and R⁷ is C1-C₆₋ᵥ alkyl, or is an aryl, alkylaryl, arylalkyl or alkylarylalkyl group containing up to (10-v) carbon atoms;

or R² and R³ taken together represent a residue of a diol or a dithiol;

A is a group of the formula:

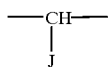

where J is

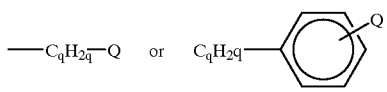

wherein Q=amino, amidino, imidazole, guanidino, $N_3$, or isothioureido, and q is an integer of from 1 to 5, or is a group of the formula

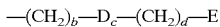

wherein
b, c and d are as defined in claim 12;
D is O; and
E is H, $C_1$–$C_6$ alkyl, $C_1$–$C_6$ haloalkyl, $C_1$–$C_6$ trialkylsilyl or $C_6$–$C_{10}$ aryl optionally substituted by up to three groups selected from $C_1$–$C_4$ alkyl, halogen and $C_1$–$C_4$ alkoxy, and
W comprises a sequence of up to 9 natural or unnatural amino acids, wherein at least one amino acid has a hydrophobic side chain.

53. A compound of claim 52, wherein W-ψ- is a group of the formula

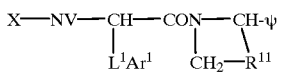

wherein $Ar^1$ is selected from the group consisting of H; phenyl; phenyl substituted by halogen, a $C_1$–$C_6$ group which is alkyl or alkyl substituted or interrupted by a carbonyl or carbonyloxy group (e.g., alkylcarbonyl or alkoxycarbonyl) or substituted by —$R^{14}$ or —$OR^{14}$ wherein $R^{14}$ is a 5- or 6-membered aromatic or non-aromatic ring or is $C_1$–$C_4$ alkyl substituted by such a 6-membered ring; bipyridyl; furanyl; chromanyl; quinolinyl; thienyl; pyridyl; α- or β-naphthyl; thionaphthyl; indolyl; p-iodophenylalanyl; diphenyl-methyl; fluorenyl; wholly or partially saturated groups corresponding to any of these; $Me_3Si$; or 2,2,2-trichloroethyl; any of the foregoing groups optionally being substituted by up to three groups selected from $C_1$–$C_3$ alkyl, $C_1$–$C_3$ alkoxy, $R^{13a}CO$— wherein $R^{13a}$ is H, $CH_3$ or $C_2H_5$, $R^{13a}OR^{1a}$— or $R^{13a}COR^{1a}$—, wherein $R^{1a}$ is —$CH_2$—, —$C_2H_4$— or —$C_3H_6$—, $L^1$ is selected from the group consisting of $CH_2$, $CH_2$—$CH_2$, O—$CH_2$, S—$CH_2$, and a bond, and V is H, or —NHV and one of $Ar^1$-$L^1$ and $Ar^2$-$L^2$ together form a group of the formula

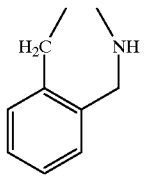

and

X is H or an amino protecting group and is bonded to the amino group of the N-terminal amino acid;

$R^{11}$ is —$CH_2$—, —$CH_2$—$CH_2$, —S—$CH_2$—, —S—C$(CH_3)_2$— or —$CH_2$—$CH_2$—$CH_2$—, which group is optionally substituted at one or more —$CH_2$— groups by from 1 to 3 $C_1$–$C_3$ alkyl groups; and ψ is —$CO_2$— or —$CH_2O$—.

54. A method of inhibiting a serine protease comprising contacting the serine protease with a compound of claim 12 or 26, wherein the compound has a P1 residue with affinity for a specificity pocket of the enzyme and a subsite binding domain with affinity for a binding site of the enzyme.

55. A method of inhibiting coagulation in an extracorporeal blood loop established for a patient comprising administering to the patient an amount of a compound of claim 12 or 26 effective to inhibit coagulation.

56. A method of inhibiting coagulation of blood in a container comprising contacting the blood with an amount of a compound of claim 12 or 26 effective to inhibit coagulation.

* * * * *

UNITED STATES PATENT AND TRADEMARK OFFICE
CERTIFICATE OF CORRECTION

PATENT NO.    : 6,127,340
DATED         : October 3, 2000
INVENTOR(S)   : Donovan St. Clair Green, et al.

It is certified that error appears in the above-identified patent and that said Letters Patent is hereby corrected as shown below:

On the Title Page:
Column 1,
On the line following the heading: "Foreign Application Priority Data", delete "9502985" and insert therefor --9502985.6--.

Column 2,
Under the heading: "FOREIGN PATENT DOCUMENTS", after the line:
"9525427  8/1996  WIPO  CO7K 5/06" insert:
          --OTHER PUBLICATIONS Elgency, S., et al., "New peptide boronic acid inhibitors of thrombin," *Adv. Exp. Med. Biol.*, 340:173-178 (1993).

In the Claims:
Claim 12, Column 43,
Line 35, delete "—HN—C($W^1$)($W^2$)—C—" and insert therefor -- —HN —C($W^1$)($W^2$)—CO— --.

Claim 20, column 46,
Line 5, delete comma after "COOH" and insert comma after "VIII".

Claim 40, Column 47,
Line 47, after "claim 12 and" please insert --$G^1$ and--.

UNITED STATES PATENT AND TRADEMARK OFFICE
CERTIFICATE OF CORRECTION

PATENT NO. : 6,127,340
DATED : October 3, 2000
INVENTOR(S) : Donovan St. Clair Green, et al.

It is certified that error appears in the above-identified patent and that said Letters Patent is hereby corrected as shown below:

Claim 42, Column 47,
Line 63, after "2 or 3" insert --,--.

Claim 45, Column 48,
Line 28-29, in the formula, delete "wherein".

Signed and Sealed this

Nineteenth Day of June, 2001

*Attest:*

*Attesting Officer*

NICHOLAS P. GODICI
*Acting Director of the United States Patent and Trademark Office*